United States Patent
Horiuchi et al.

(10) Patent No.: US 8,829,503 B2
(45) Date of Patent: Sep. 9, 2014

(54) CONDENSED POLYCYCLIC COMPOUND AND ORGANIC LIGHT EMITTING ELEMENT INCLUDING THE SAME

(75) Inventors: Takayuki Horiuchi, Tokyo (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 151 days.

(21) Appl. No.: 13/591,003

(22) Filed: Aug. 21, 2012

(65) Prior Publication Data

US 2013/0048966 A1 Feb. 28, 2013

(30) Foreign Application Priority Data

Aug. 23, 2011 (JP) ................. 2011-181581

(51) Int. Cl.
*H01L 35/24* (2006.01)
(52) U.S. Cl.
USPC ................... 257/40; 257/E51.001
(58) Field of Classification Search
USPC .......................... 257/40, E51.001
See application file for complete search history.

(56) References Cited

FOREIGN PATENT DOCUMENTS

| CN | 101432249 A | 5/2009 |
|---|---|---|
| JP | 10-330295 A | 12/1998 |
| JP | 2011-011994 A | 1/2011 |
| WO | 2008137995 A | 11/2008 |
| WO | 2008137995 A1 | 11/2008 |

OTHER PUBLICATIONS

Von Helden et al., "Resonant Ionization Using IR Light: A New Tool to Study the Spectroscopy and Dynamics of Gas-Phase Molecules and Clusters", J. Phys. Chem. A., Mar. 20, 2003, vol. 107, No. 11, pp. 1671-1688.
Jiang et al., "The Linear Optical Polarizability Spectra of Five C78 Isomers", Communications in Theoretical Physics, Jul. 30, 1999, vol. 32, No. 1, pp. 37-42, Beijing, China.

*Primary Examiner* — Anthony Ho
(74) *Attorney, Agent, or Firm* — Canon U.S.A., Inc., IP Division

(57) ABSTRACT

An organic light emitting element which realizes a high efficiency and a long light emission life is provided. An organic compound represented by the general formula [1] described in Claim 1 is provided. In the formula [1], $R_1$ to $R_{22}$ are each independently selected from the group consisting of a hydrogen atom, a substituted or unsubstituted alkyl group, a substituted or unsubstituted aryl group, and a substituted or unsubstituted heterocyclic group.

14 Claims, 2 Drawing Sheets

CONDENSED POLYCYCLIC COMPOUND AND ORGANIC LIGHT EMITTING ELEMENT INCLUDING THE SAME

BACKGROUND OF THE INVENTION

1. Field of the Invention

The present invention relates to a condensed polycyclic compound and an organic light emitting element including the same.

2. Description of the Related Art

An organic light emitting element is an element which has an anode, a cathode, and an organic compound layer arranged between these two electrodes.

In the organic light emitting element, an exciton is generated when a hole and an electron, which are injected from the respective electrodes, are recombined with each other in the organic compound layer, and light is emitted when the exciton returns to the ground state. The organic light emitting element is also called an organic electroluminescent element or an organic EL element.

The recent advances in the organic light emitting element are remarkable, and a high-speed response, thin, and light-weight light emitting device which can be driven at a low voltage and which has various light emitting wavelengths can be formed.

Heretofore, creation of luminescent organic compounds has been energetically carried out. The reason for this is that in order to provide a high-performance organic light emitting element, creation of a compound having excellent light emitting properties is important.

Japanese Patent Laid-Open No. 10-330295 has disclosed a condensed polycyclic compound which has the following dibenzo[f,f']diindeno[1,2,3-cd:1',2',3'-lm]perylene (A-1) as a basic skeleton and which emits red light.

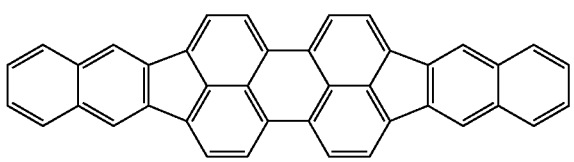

A-1

The compound disclosed in the above patent document is a compound which emits light in a red spectrum region. However, the light emitting efficiency and the color purity of the above compound are not sufficient to be used for an organic light emitting element.

SUMMARY OF THE INVENTION

Aspects of the present invention provide a condensed polycyclic compound which emits light having a high color purity with a high efficiency in a red spectrum region. In addition, aspects of the present invention also provide an organic light emitting element having a high light emitting efficiency and a long element life.

Accordingly, aspects of the present invention provides a condensed polycyclic compound represented by the following general formula [1].

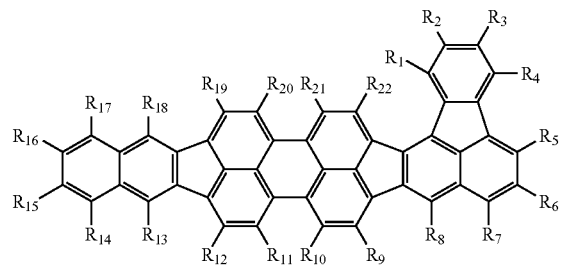

[1]

In the formula [1], $R_1$ to $R_{22}$ are each independently selected from the group consisting of a hydrogen atom, a substituted or unsubstituted alkyl group, a substituted or unsubstituted aryl group, and a substituted or unsubstituted heterocyclic group.

According to aspects of the present invention, a condensed polycyclic compound which emits light having a high color purity with a high efficiency in a red spectrum region can be provided. In addition, an organic light emitting element which includes the above compound and which has a high light emitting efficiency and a long element life can be provided.

Further features of the present invention will become apparent from the following description of exemplary embodiments with reference to the attached drawings.

DESCRIPTION OF THE EMBODIMENTS

Figure 1:
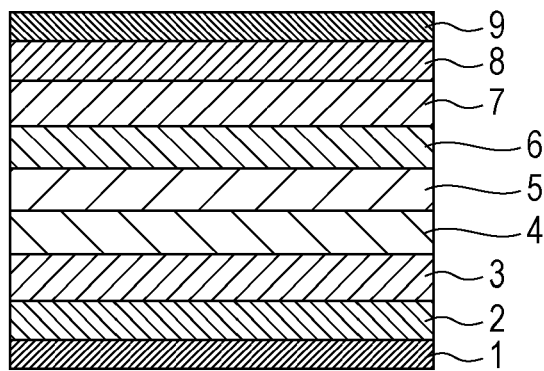
FIG. 1 is a schematic view of one example of a multilayer type organic light emitting element according to the embodiment.

Aspects of the present invention relate to a condensed polycyclic compound represented by the following general formula [1].

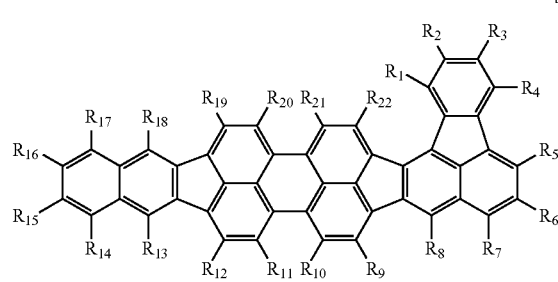

[1]

In the formula [1], $R_1$ to $R_{22}$ are each independently selected from the group consisting of a hydrogen atom, a substituted or unsubstituted alkyl group, a substituted or unsubstituted aryl group, and a substituted or unsubstituted heterocyclic group.

As the alkyl groups represented by $R_1$ to $R_{22}$, although a methyl group, an ethyl group, a normal propyl group, an isopropyl group, a normal butyl group, a secondary butyl group, a tertiary butyl group, a cyclohexyl group, an octyl group, a 1-adamantyl group, and a 2-adamantyl group may be mentioned by way of example, of course, the alkyl groups are not limited thereto.

As the aryl groups represented by $R_1$ to $R_{22}$, although a phenyl group, a naphthyl group, an indenyl group, a biphenyl group, a terphenyl group, and a fluorenyl group may be mentioned by way of example, of course, the aryl groups are not limited thereto.

As the heterocyclic groups represented by $R_1$ to $R_{22}$, although a pyridyl group, a quinolyl group, an oxazolyl group, a thiazolyl group, a carbazolyl group, an acridinyl group, a phenanthrolyl group, a thienyl group, and a pyrimidinyl group may be mentioned by way of example, of course, the heterocyclic groups are not limited thereto.

As substituents which the aryl group and the heterocyclic group may further have, for example, there may be mentioned an alkyl group, such as a methyl group, an ethyl group, a normal propyl group, an isopropyl group, a normal butyl group, or a tertiary butyl group; an aralkyl group, such as a benzyl group; an aryl group, such as a phenyl group or a biphenyl group; a heterocyclic group, such as a pyridyl group or a pyrrolyl group; an amino group, such as a dimethylamino group, a diethylamino group, a dibenzylamino group, a diphenylamino group, or a ditolylamino group; alkoxy groups, such as a methoxy group, an ethoxy group, and a propoxy group; an aryloxy group, such as a phenoxy group; a halogen atom, such as fluorine, chlorine, bromine, or iodine; and a cyano group; however, of course, the substituents are not limited thereto.

(Substituent Introduced on Condensed Polycyclic Compound According to Aspects of the Present Invention)

A basic skeleton of the condensed polycyclic compound according to aspects of the present invention is a basic skeleton having high planarity. When an alkyl group, an aryl group, and/or a heterocyclic group is substituted as a substituent on a compound having a high planarity, the solubility to a solvent and the sublimability in vacuum deposition are improved.

In this embodiment, the basic skeleton indicates a partial structure having the largest π conjugated structure in the compound molecule.

This structure is a structure which primarily determines the physical properties of the whole compound, such as the S1 energy, the T1 energy, the HOMO level, the LUMO level, the oscillator strength, and the light emitting quantum yield.

In addition, when the above substitute is provided, the molecular association in a solid state can also be suppressed. Furthermore, in the case in which the condensed polycyclic compound according to aspects of the present invention is used as a light emitting material of an organic light emitting element, the substituent may be substituted on the above compound since the concentration quenching is suppressed.

The effect as described above can be significantly enhanced when an alkyl group is further substituted on an aryl group or a heterocyclic group.

As the substituent substituted on the condensed polycyclic compound according to aspects of the present invention, in one case a substituent including no heteroatoms, that is, an alkyl group or an aryl group, may be provided.

The reason for this is that since the charge is localized in a heterocyclic group due to the difference in electronegativity between a carbon atom and a heteroatom, which form the heterocyclic group, the reactivity thereof to an electrophilic agent or a nucleophilic agent is high as compared to that of an alkyl group or an aryl group.

The condensed polycyclic compound according to aspects of the present invention has a skeleton in which indene is condensed to a dibenzo[f,f']diindeno[1,2,3-cd:1',2',3'-lm]perylene skeleton.

Accordingly, the planarity of the condensed polycyclic compound according to aspects of the present invention is higher than that of the dibenzo[f,f']diindeno[1,2,3-cd:1',2',3'-lm]perylene skeleton.

Since improvement in sublimability and suppression of concentration quenching can be achieved, substituents may be substituted at this condensed indene portion, that is, $R_1$ to $R_4$ in the formula [1].

In addition, $R_5$, $R_6$, $R_{15}$, and $R_{16}$ in the formula [1] are located in a major axis direction of the plane of the basic skeleton. The crystallinity can be reduced when substituents are substituted at the above positions.

On the other hand, since $R_8$ to $R_{13}$ and $R_{18}$ to $R_{22}$ in the formula [1] are located in the vicinity of the center of the basic skeleton, when substituents are substituted at these positions, an effect of reducing the crystallinity may be enhanced.

In this structure, $R_8$, $R_{13}$, and $R_{28}$ receive strong steric hindrance from $R_7$ and $R_9$, $R_{12}$ and $R_{14}$, and $R_{17}$ and $R_{19}$, respectively.

Hence, when an aryl group or a heterocyclic group is substituted at $R_8$, $R_{13}$, and $R_{18}$, the plane of the substituent is arranged orthogonal to the plane of the basic skeleton due to steric repulsion by the surrounding hydrogen atom or substituent. As a result, it may be preferable since the molecular association between the planes of the basic skeletons is suppressed.

In addition, when the molecular weight is increased to approximately 1,000 by introduction of many substituents on the condensed polycyclic compound, the sublimability is degraded.

Hence, when the condensed polycyclic compound according to aspects of the present invention is used by vacuum deposition, in order to suppress an increase in molecular weight, a smaller number of substituents substituted on the basic skeleton may be provided.

In addition, in the condensed polycyclic compound according to aspects of the present invention, when $R_7$, $R_9$ to $R_{12}$, $R_{14}$, $R_{17}$, and $R_{19}$ to $R_{22}$ are hydrogen atoms, it may be preferable since the sublimability of the compound is improved.

Furthermore, in particular, $R_5$ to $R_7$, $R_9$ to $R_{12}$, $R_{14}$ to $R_{17}$, and $R_{19}$ to $R_{22}$ may be hydrogen atoms. The reason for this is that the sublimability of the compound is high.

(Properties of Condensed Polycyclic Compound According to Aspects of the Present Invention)

Fluorescence emission properties of a diluted solution of the compound disclosed in Japanese Patent Laid-Open No. 10-330295 (referred to as "Compound 1" in this embodiment) and an example compound B-1 which is the condensed polycyclic compound according to aspects of the present invention were measured.

TABLE 1

| | STRUCTURE | EMISSION PEAK WAVELENGTH | CHROMATICITY | QUANTUM YIELD |
|---|---|---|---|---|
| COMPOUND 1 | (structure) | 597 nm | (0.63, 0.37) | 0.62 |
| EXAMPLE COMPOUND B-1 | (structure) | 605 nm | (0.65, 0.35) | 0.77 |

The compound 1 and the example compound B-1 both exhibited red light emission having an emission peak wavelength of approximately 600 nm.

The red light in this embodiment indicates light having a maximum peak wavelength of the emission spectrum of 590 to 630 nm.

As the index of emission color, the CIE chromaticity coordinates (X, Y) are generally used. The red in accordance with the NTSC standard is (0.67, 0.33), and a value closer thereto indicates a higher color purity.

When the chromaticity of the compound 1 and that of the example compound B-1 each obtained from the fluorescence spectrum were compared to each other, the red of the example compound B-1 was closer to the NTSC standard. That is, a higher color purity was obtained.

Since it is supposed that the effects of the substituent to the emission wavelength of these two compounds are approximately equal to each other, the difference in the measured chromaticity results from the difference in basic skeleton between the two compounds.

Furthermore, when the emission quantum yields of the above two compounds were compared to each other, the value of the example compound B-1 was 1.24 times the value of the compound 1. A light emitting material having a high quantum yield is useful to an organic light emitting element having a high light emitting efficiency.

When these results are collectively taken into consideration, the condensed polycyclic compound according to aspects of the present invention can exhibit red light emission having a high color purity and a high efficiency as compared to those of a related compound.

Accordingly, the condensed polycyclic compound according to aspects of the present invention can be used as a red light emitting material of an organic light emitting element.

Next, the effect of the five-membered ring of the condensed polycyclic compound according to aspects of the present invention will be described.

When only this five-membered ring is considered, it is found that five π electrons are present therein.

When an electron moves to the condensed polycyclic compound according to aspects of the present invention from a cathode, an electron transport material, or the like in an organic light emitting element, since a 6π-electron system which satisfies Huckel's rule is formed in the five-membered ring, the five-membered ring is stabilized to a certain degree which corresponds to the resonance energy.

That is, the HOMO/LUMO levels of a condensed polycyclic compound having a five-membered ring are lowered as compared to those of a compound having no five-membered ring if the energy gaps thereof are equal to each other.

Since the condensed polycyclic compound according to aspects of the present invention has three five-membered rings, the HOMO/LUMO levels are further lowered as compared to those of the compound 1.

Hence, when the condensed polycyclic compound according to aspects of the present invention loses an electron at the HOMO level, relatively high energy is required.

That is, the condensed polycyclic compound according to aspects of the present invention is chemically stable to an oxidizing agent, such as oxygen.

Hence, the condensed polycyclic compound according to aspects of the present invention is rarely denatured by oxidation in manufacturing and/or refining, and a material having a high purity can be used for an organic light emitting element, so that an element having a longer life can be formed.

In addition, when the condensed polycyclic compound according to aspects of the present invention is used as a guest material of a light emitting layer, since the LUMO level is low, electrons of the light emitting layer can be strongly trapped.

Consequently, since electrons are confined in the light emitting layer, recombination with holes primarily occurs in the light emitting layer, and an improvement in efficiency of an organic light emitting element can be achieved.

Accordingly, as a result, the condensed polycyclic compound according to aspects of the present invention can emit light having a high color purity with a high efficiency in a red spectrum region. In addition, an organic light emitting element having a high light emitting efficiency and a long element life can be formed using the condensed polycyclic compound according to aspects of the present invention.

(Examples of Condensed Polycyclic Compound According to Aspects of the Present Invention)

Examples of the condensed polycyclic compound according to aspects of the present invention will be shown below as an A group to a C group.

A-1

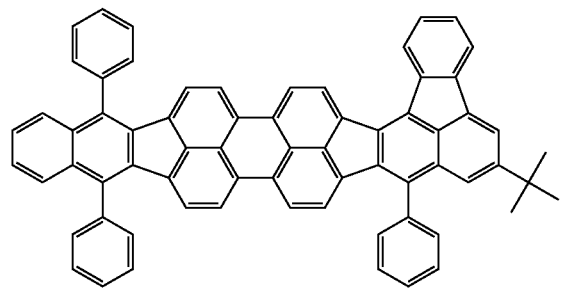

A-2

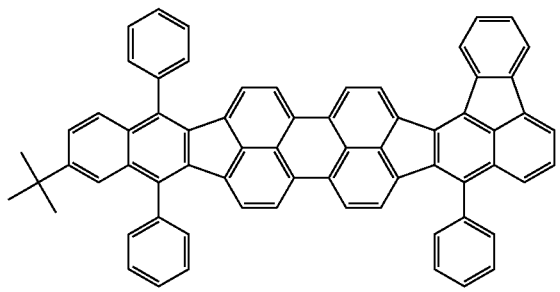

A-3

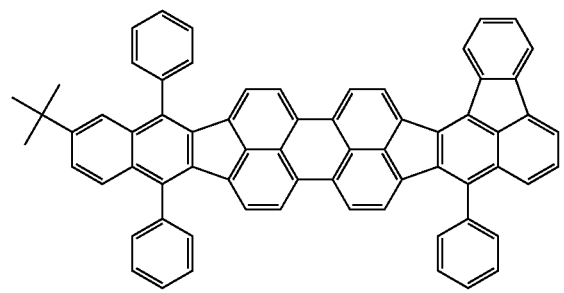

A-4

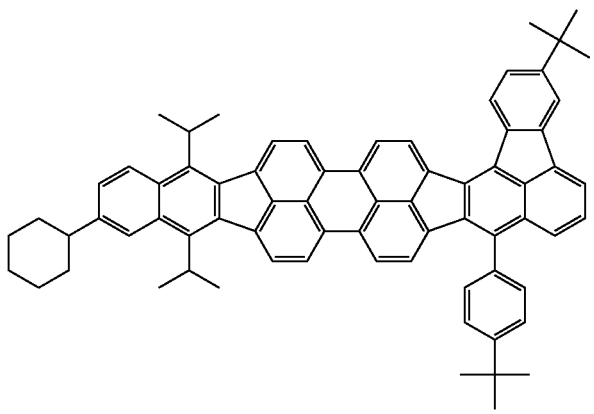

A-5

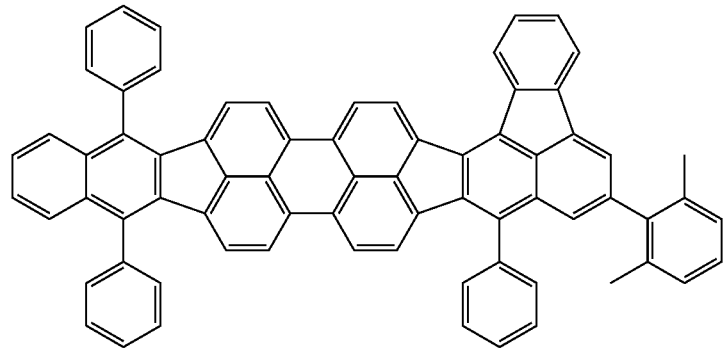

A-6
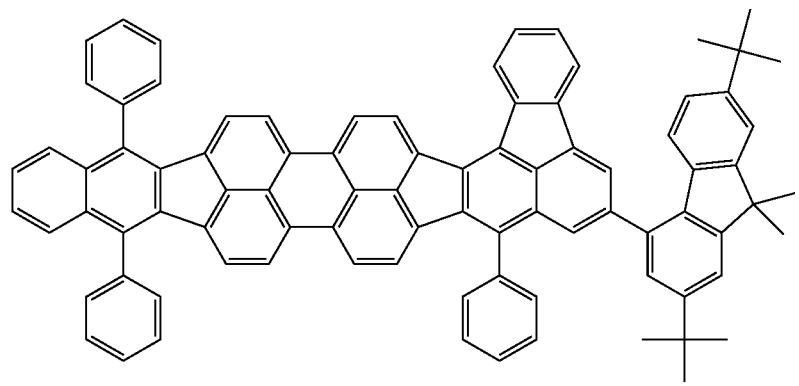
A-7
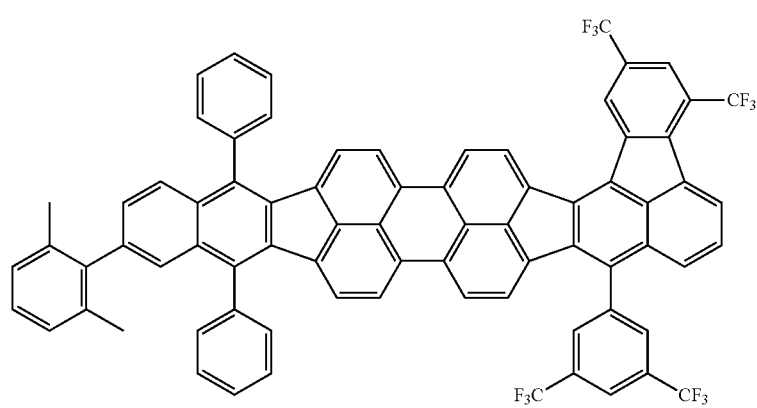
A-8
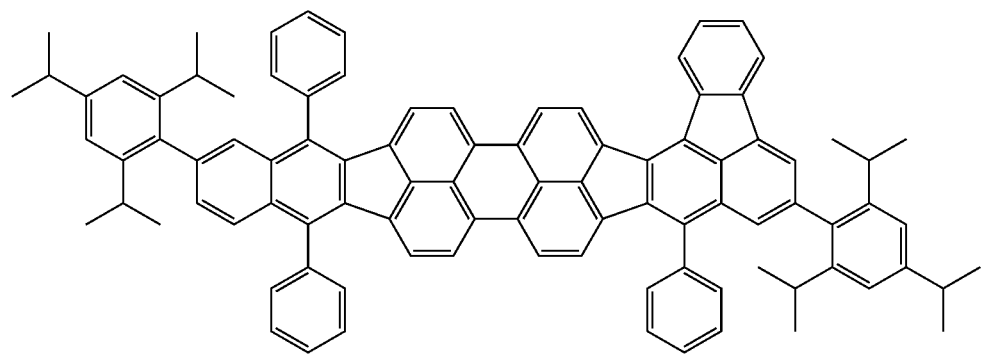
A-9
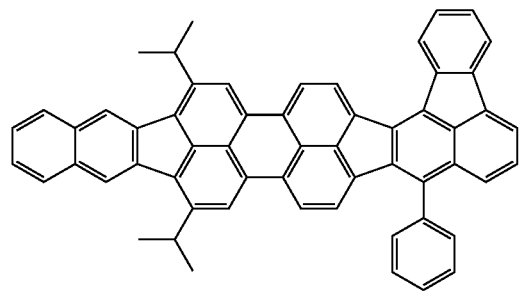
A-10
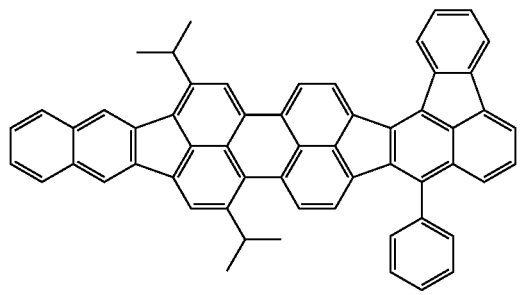

-continued
A-11
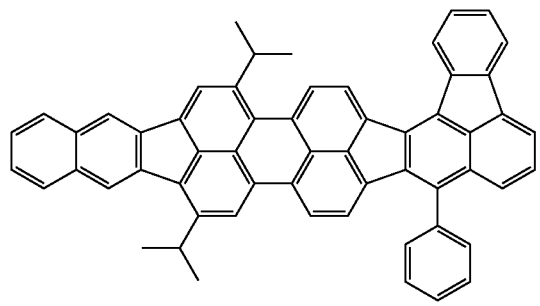
A-12
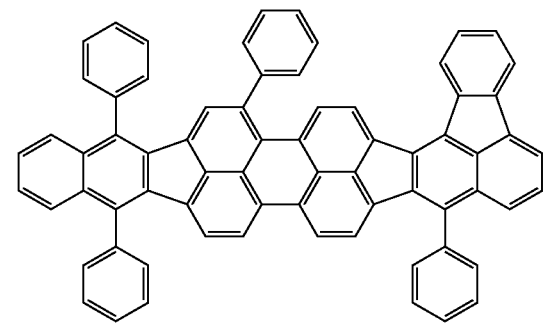
A-13
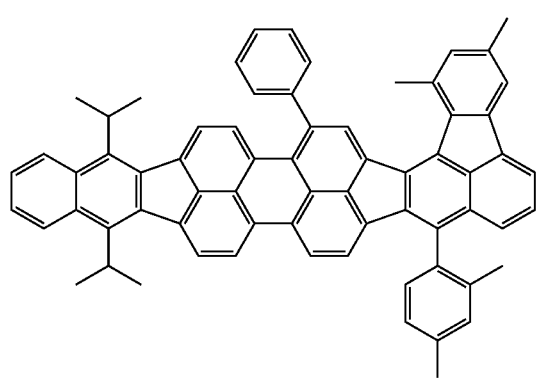
A-14
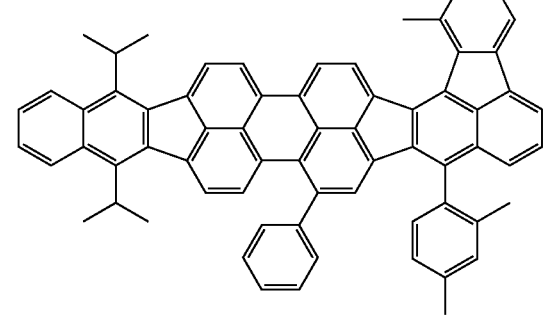
A-15
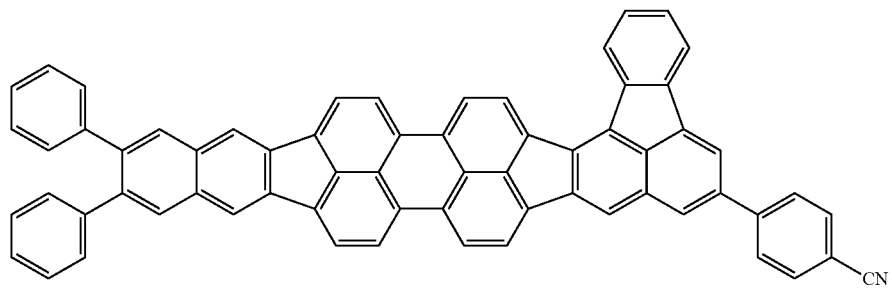
A-16
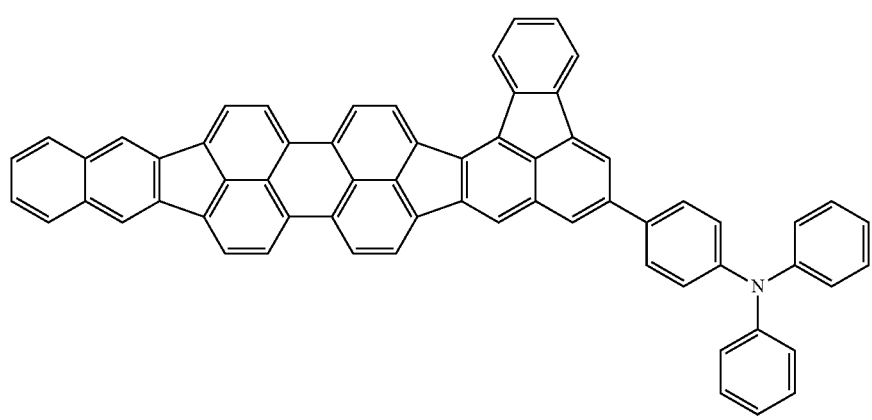

-continued
A-17
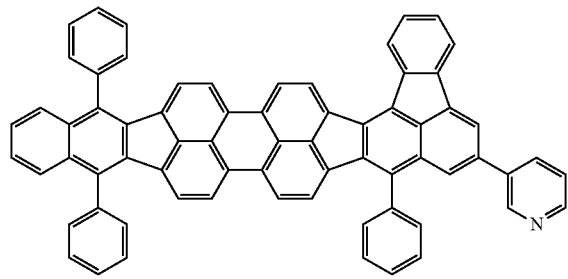
A-18
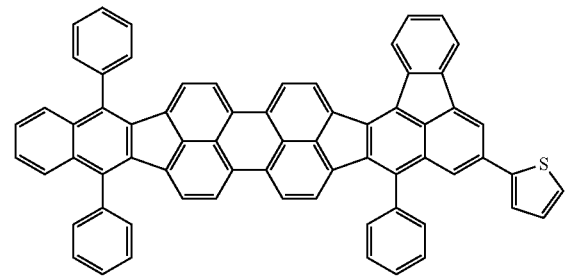
B-1
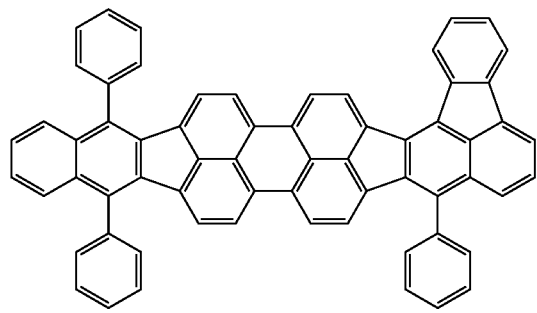
B-2
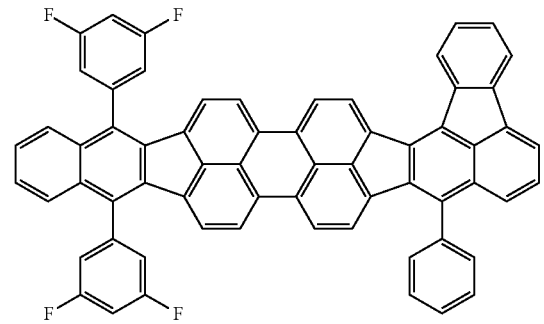
B-3
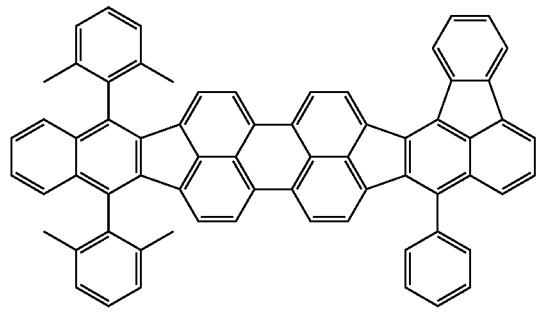
B-4
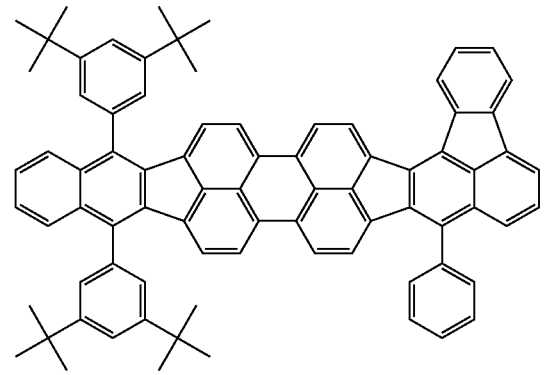
B-5
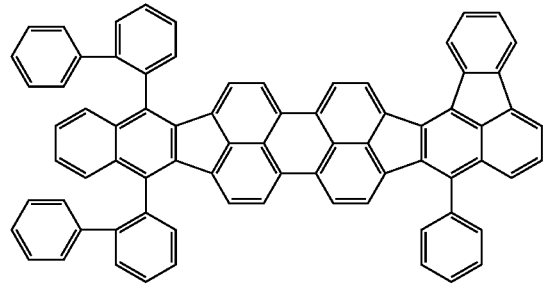
B-6
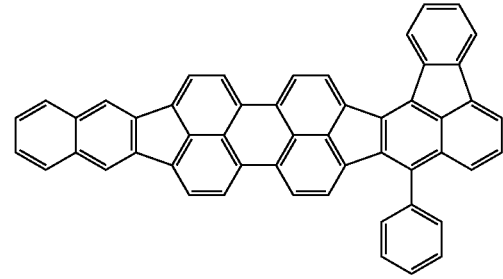

-continued
B-7
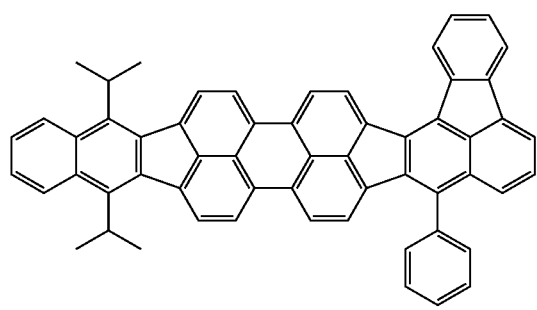
B-8
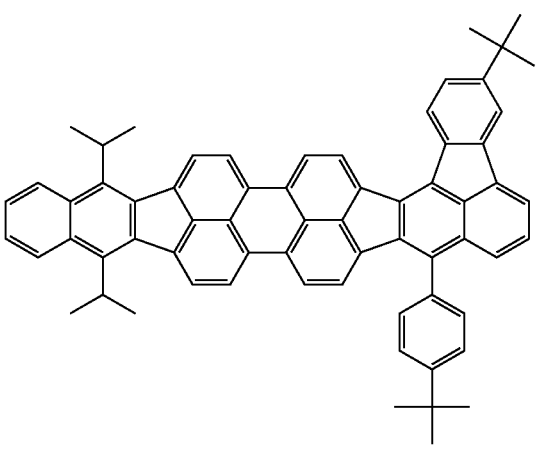
B-9
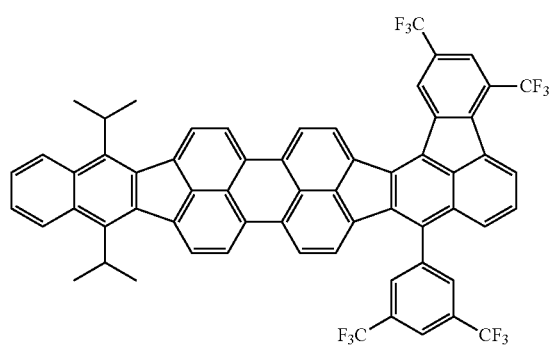
B-10
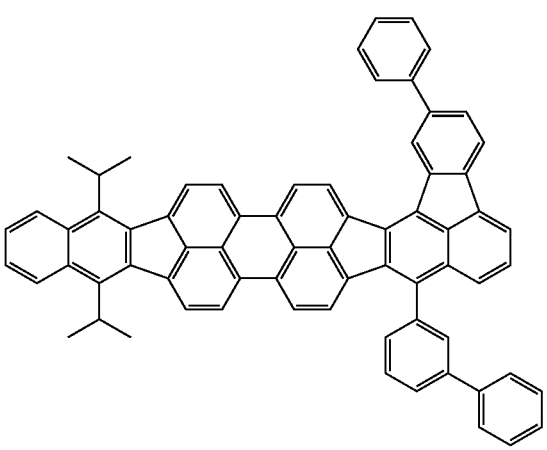
B-11
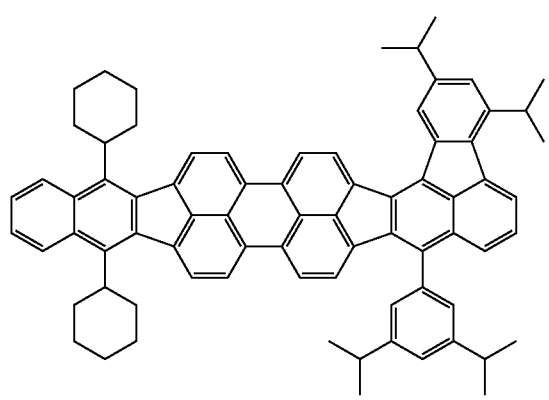
B-12
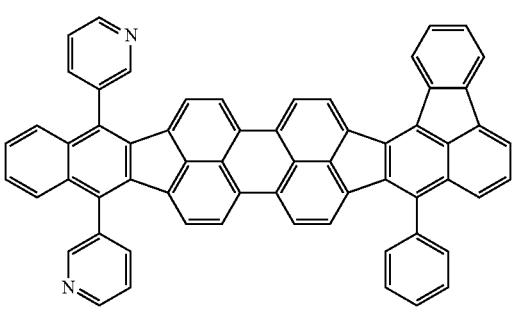 [SMILES: c1ccc(-c2c3c(c(-c4ccccc4)c4ccccc24)-c2ccc4c5ccc6c7c(ccc(c8ccc-3c2c84)c57)c2c(-c3ccccc3)c3cccc4c5ccccc5c(c34)c62)cc1]
C-1
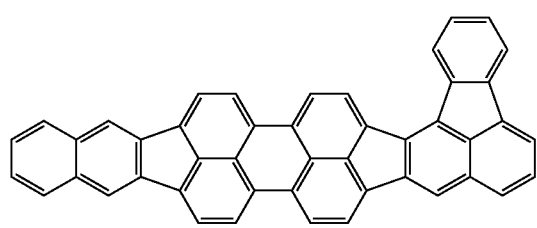
C-2
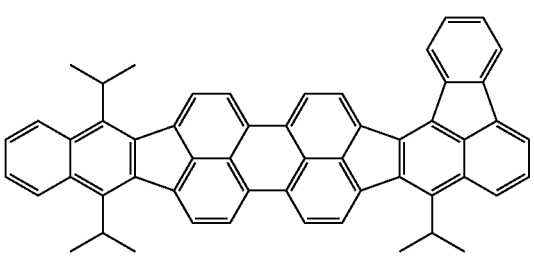

-continued

C-3

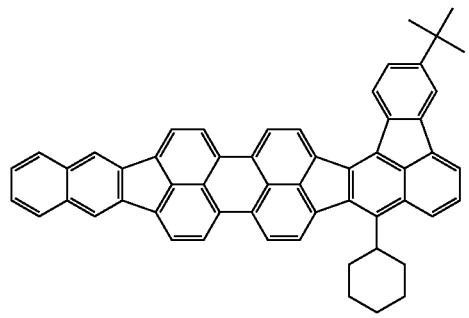

C-4

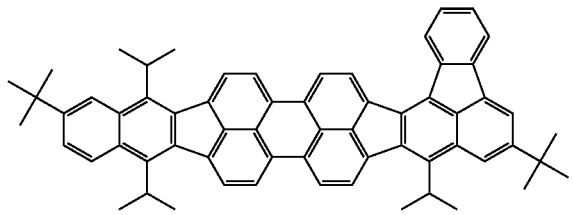

C-5

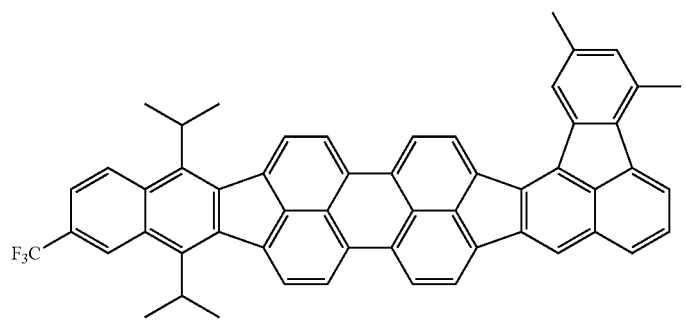

(Properties of Respective Example Compounds)

The example compounds shown in the A group are each a compound having at least one substituent substituted at at least one of $R_1$ to $R_{22}$ in the formula [1]. Fine adjustment of the properties can be performed by various changing the position and the type of the substituent.

The example compounds shown in the B group are each a compound in which $R_5$ to $R_7$, $R_9$ to $R_{12}$, $R_{14}$ to $R_{17}$, and $R_{19}$ to $R_{22}$ in the formula [1] indicate hydrogen atoms, and at least one substituent is substituted at at least one of $R_1$ to $R_4$, $R_8$, $R_{13}$, and $R_{18}$. These compounds each have a structure having a good balance between the sublimability and suppression of molecular association.

The example compounds shown in the C group are each a compound in which $R_1$ to $R_{22}$ in the formula [1] all indicate hydrogen atoms, or substituted or unsubstituted alkyl groups are substituted at at least two of $R_1$ to $R_{22}$. Since these compounds each have a small molecular weight, the sublimability thereof is excellent.

(Description of Synthetic Route)

A synthetic route of the condensed polycyclic compound according to aspects of the present invention will be described using the example compound B-1 as one example. A synthetic scheme will be described below.

First, a benzofluoranthene bromo compound is synthesized by the following route.

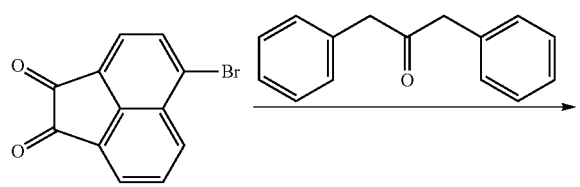

-continued

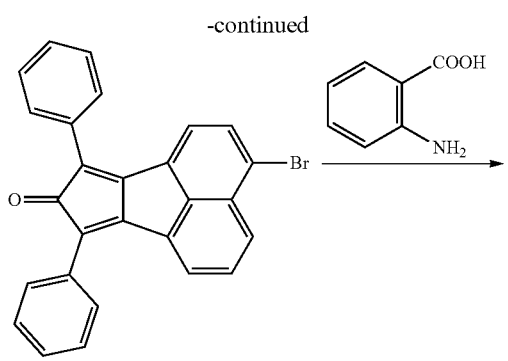

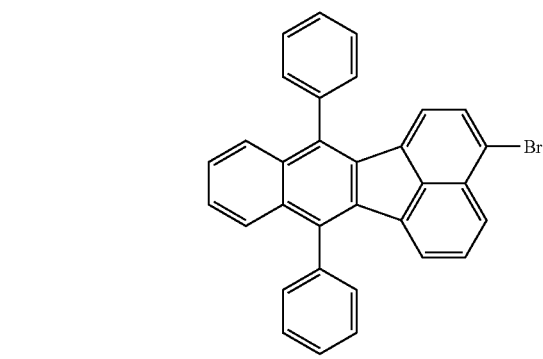

Next, an acenaphthofluoranthene bromo compound is synthesized by the following route.

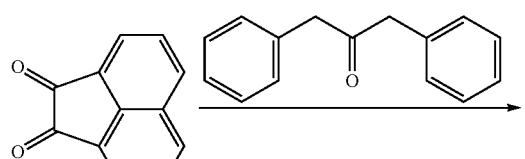
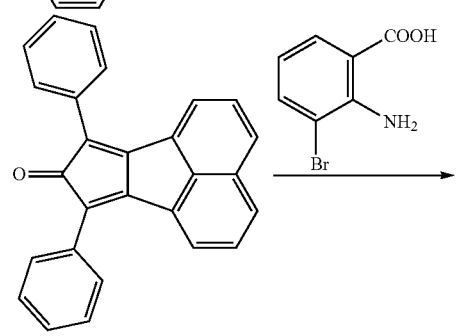
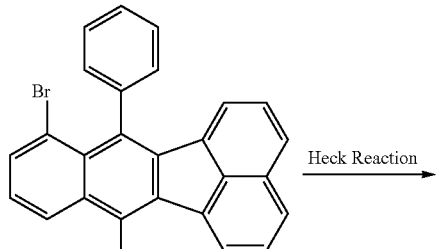
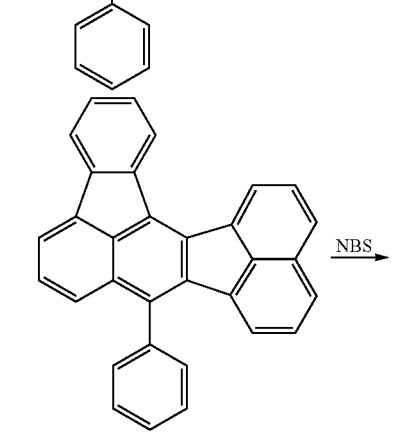
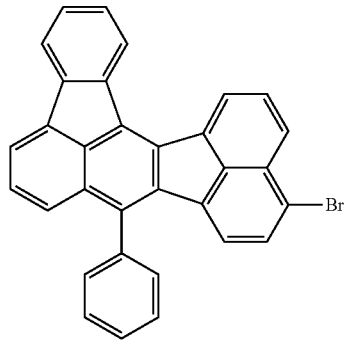

After one of the benzofluoranthene bromo compound and the acenaphthofluoranthene bromo compound thus obtained was converted into a boronic acid derivative, a Suzuki cross coupling reaction is performed ($X_1$=Br, $X_2$=B(OH)$_2$ or an ester thereof, or $X_1$=B(OH)$_2$ or an ester thereof, $X_2$=Br).

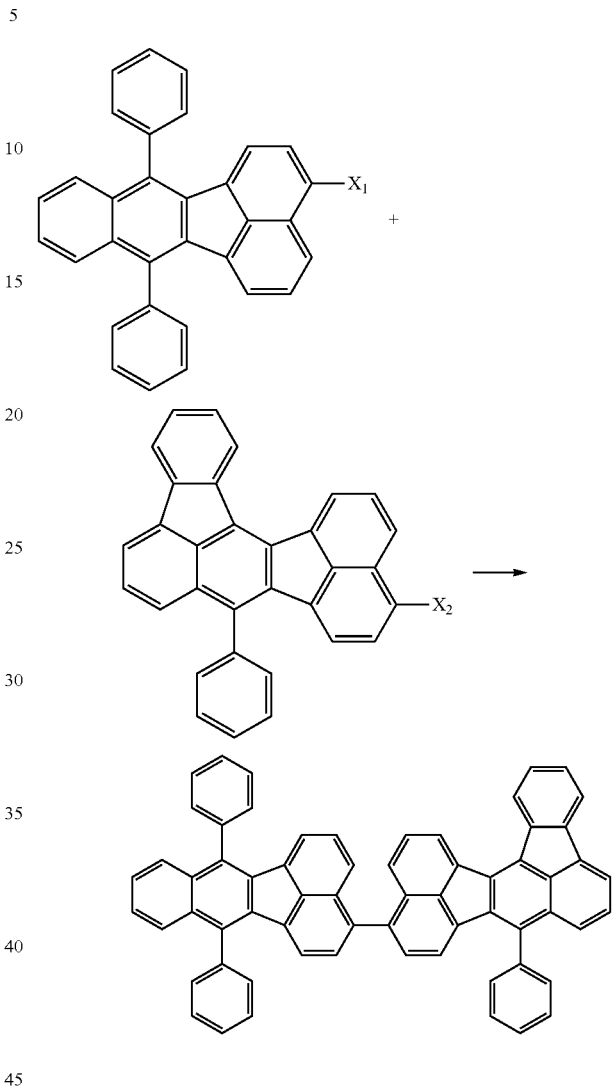

When the obtained coupled compound is allowed to react with 2,3-dichloro-5,6-dicyano-1,4-benzoquinone (DDQ) or a strong base, such as tertiary butoxy potassium, a cyclization reaction occurs, so that the condensed polycyclic compound according to aspects of the present invention is obtained.

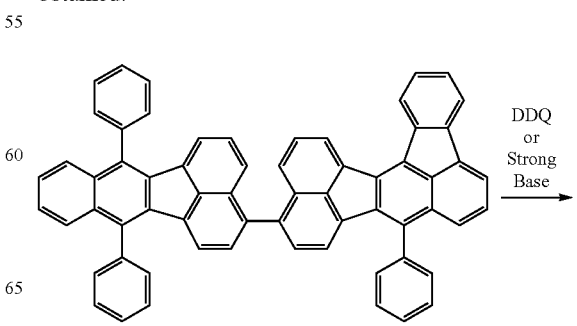

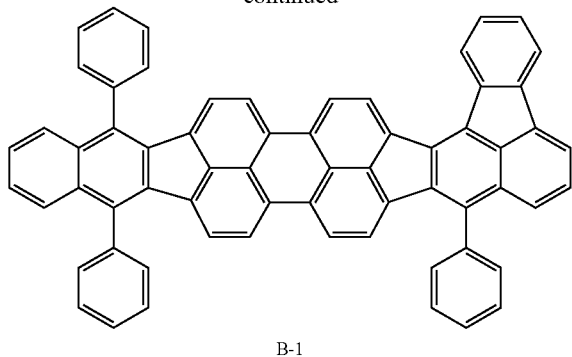

B-1

When a substituent is introduced at a different position, introduction may be performed at the stage of a raw material or an intermediate or may also be performed after the basic skeleton is formed.

(Properties of Organic Light Emitting Element According to this Embodiment)

Next, an organic light emitting element according to this embodiment will be described.

The organic light emitting element according to the this embodiment is a light emitting element at least including an anode, a cathode, which are a pair of electrodes, and an organic compound layer arranged between these electrodes.

In the organic light emitting element according to this embodiment, as long as a light emitting layer is included, the organic compound layer may be a single layer or a laminate having a plurality of layers.

When the organic compound layer is a laminate having a plurality of layers, besides the light emitting layer, the organic compound layer may includes layers which are appropriately selected from a hole injection layer, a hole transport layer, an electron block layer, a hole/exciton block layer, an electron transport layer, an electron injection layer, and the like. In addition, the light emitting layer may be a single layer or a laminate having a plurality of layers.

The structure of the organic light emitting element according to this embodiment is not limited thereto.

Various layer structures can be formed, and for example, an insulating layer may be provided at an interface between the electrode and the organic compound layer, an adhesive layer or an interference layer may be provided, and/or the electron transport layer or the hole transport layer may be formed from two layers having different ionization potentials.

As an element configuration of the above structures, a so-called top emission system in which light is extracted from a side opposite to the substrate, a so-called bottom emission system in which light is extracted from a substrate side, and a dual emission system in which light is extracted from both surface sides may be used.

In the organic light emitting element according to this embodiment, the condensed polycyclic compound according to aspects of the present invention is contained in at least one layer of the organic compound layer.

In particular, the condensed polycyclic compound according to aspects of the present invention is contained in at least one of a hole injection layer, a hole transport layer, an electron block layer, a light emitting layer, a hole/exciton block layer, an electron transport layer, an electron injection layer, and the like.

The condensed polycyclic compound according to aspects of the present invention may be contained in the light emitting layer.

In the organic light emitting element according to this embodiment, when the condensed polycyclic compound according to aspects of the present invention is contained in the light emitting layer, the light emitting layer may be a layer including only the condensed polycyclic compound according to aspects of the present invention or may be a layer including the condensed polycyclic compound according to aspects of the present invention and at least one another compound.

When the light emitting layer is a layer including the condensed polycyclic compound according to aspects of the present invention and at least one another compound, the condensed polycyclic compound according to aspects of the present invention may be used as a host material of the light emitting layer or may be used as a guest material thereof. In addition, the condensed polycyclic compound according to aspects of the present invention may also be used as an assistant material contained in the light emitting layer.

The host material in this case is a compound having the highest weight ratio among compounds forming the light emitting layer.

In addition, the guest material is a compound having a weight ratio lower than that of the host material among the compounds forming the light emitting layer and is responsible for primary light emission.

The assist material is a compound having a weight ratio lower than that of the host material among the compounds forming the light emitting layer and assists light emission of the guest material. In addition, the assist material is also called a second host material.

When the condensed polycyclic compound according to aspects of the present invention is used as the guest material of the light emitting layer, the concentration of the guest material to the whole light emitting layer may be 0.01 to 20 percent by weight, such as 0.1 to 5 percent by weight. The reason the concentration is set as described above is to suppress the concentration quenching.

The guest material may be included uniformly in the whole layer formed of the host material or may be included therein to form a concentration gradient, or the guest material may be included partially in a specific region to form a region of a host material layer containing no guest material.

In addition, when the condensed polycyclic compound according to aspects of the present invention is used as the guest material of the light emitting layer, a material having a LUMO level higher than that of the condensed polycyclic compound according to aspects of the present invention (that is, a material having a LUMO level closer to the vacuum level) used as the host material.

The reason for this is that since the condensed polycyclic compound according to aspects of the present invention has a low LUMO level, when a material having a higher LUMO level than that of the condensed polycyclic compound according to aspects of the present invention is used as the host material, the condensed polycyclic compound according to aspects of the present invention more preferably receives electrons supplied to the host material of the light emitting layer.

The light emitting layer of the organic light emitting element according to this embodiment may be a single layer or may includes a plurality of layers, and when light emitting materials having different light emission colors are contained, a plurality of emission colors may be mixed together.

In this case, the light emission color of the organic light emitting element is not limited to red. In more particular, the light emission color may be either a white or a neutral color.

In addition, as a film formation method, although a deposition method or a coating method may be mentioned by way of example, the method is not particularly limited.

On the other hand, the condensed polycyclic compound according to aspects of the present invention may be used as a constituent material of the organic compound layer other than the light emitting layer, the organic compound layer forming the organic light emitting element according to this embodiment. In particular, the condensed polycyclic compound according to aspects of the present invention may also be used as a material forming an electron transport layer, an electron injection layer, a hole transport layer, a hole injection layer, a hole block layer, and the like.

In this case, the light emission color of the organic light emitting element is not limited to red. In more particular, the light emission color may be either a white or a neutral color.

The case in which the organic light emitting element according to this embodiment emits white light will be described by way of example with reference to FIG. 1.

FIG. 1 is a schematic cross-sectional view showing one example of a laminated light emitting layer type element. Although a light emitting layer including three layers is shown by way of example, a light emitting layer including two layers may also be used.

This organic light emitting element has an element structure in which an anode 1, a hole injection layer 2, a hole transport layer 3, a blue light emitting layer 4, a green light emitting layer 5, a red light emitting layer 6, an electron transport layer 7, an electron injection layer 8, and a cathode 9 are laminated on a substrate, such as a glass. However, the lamination order of the blue, the green, and the red light emitting layers are not particularly limited.

In addition, the light emitting layers may not be restricted to be laminated to each other but may also be arranged side by side. The light emitting layers arranged side by side are each arranged so as to be in contact with the hole transport layer and the electron transport layer.

In addition, the light emitting layer may also have a structure in which in a light emitting layer which emits one color light, a domain of a light emitting layer which emits color light different therefrom is formed.

At least one of the light emitting layers contains the condensed polycyclic compound according to aspects of the present invention. This light emitting layer may be a light emitting layer which emits red light.

One example of an organic light emitting element which emits white light shown in this embodiment is an organic light emitting element which emits white light in such a way that among a plurality of light emitting layers, red light emission and light emission of a light emitting layer which emits light other than red light are mixed together.

It may also be said that the plurality of light emitting layers forms a light emitting portion.

When an organic light emitting element which emits white light is obtained, although a blue light emitting material is not particularly limited, a light emitting material having a fluoranthene skeleton or an anthracene skeleton may be provided.

In addition, although a green light emitting material is not particularly limited, a light emitting material having a fluoranthene skeleton or an anthracene skeleton may be provided.

In the organic light emitting element according to this embodiment, optionally, currently known low molecular and high molecular materials may also be used besides the condensed polycyclic compound according to aspects of the present invention.

In more particular, for example, a hole injection compound or hole transport compound, a host material or light emitting compound, or an electron injection compound or electron transport compound may also be used together.

Hereinafter, examples of these compounds will be described.

As the hole injection/transport material, a material having a high hole mobility may be provided so that holes from the anode are easily injected and injected holes can be transported to the light emitting layer.

As the low molecular and high molecular materials each having a hole injection/transport ability, for example, there may be mentioned a triarylamine derivative, a phenylenediamine derivative, a stilbene derivative, a phthalocyanine derivative, a porphyrin derivative, a poly(vinyl carbazole), a polythiophene, and other conductive polymers.

As the host material, in particular, compounds shown in the following Table 2 may be mentioned.

TABLE 2

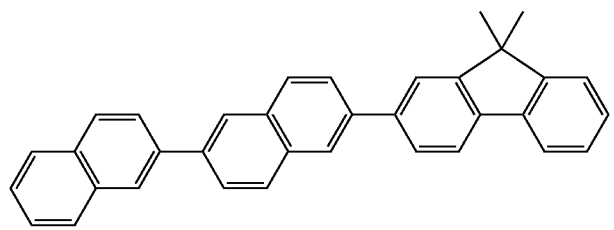 [SMILES: CC1(C)c2ccccc2-c2ccc(-c3ccc4cc(-c5ccc6ccccc6c5)ccc4c3)cc21]

H1

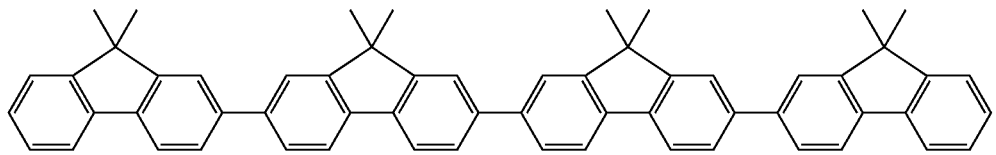 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]

H2

TABLE 2-continued
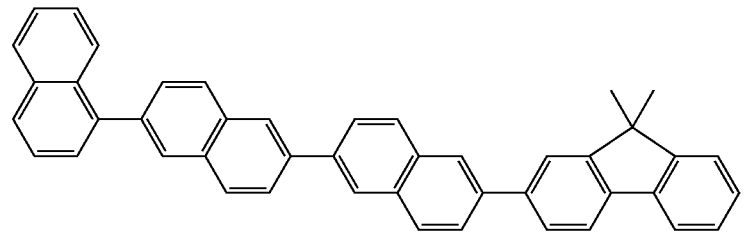 [SMILES: CC1(C)c2ccccc2-c2ccc(-c3ccc4cc(-c5ccc6cc(-c7cccc8ccccc78)ccc6c5)ccc4c3)cc21]
H3
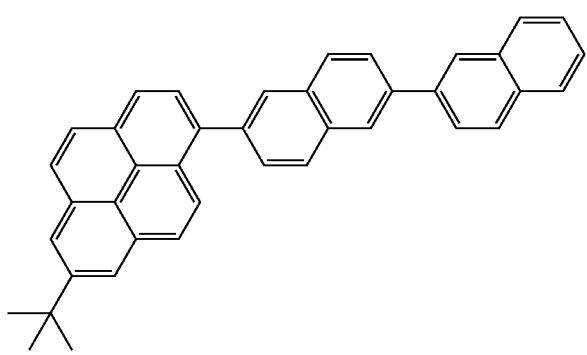 [SMILES: CC(C)(C)c1cc2ccc3ccc(-c4ccc5cc(-c6ccc7ccccc7c6)ccc5c4)c4ccc(c1)c2c34]
H4
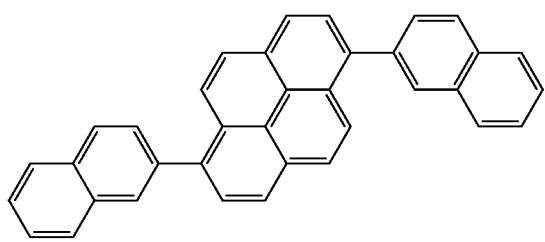 [SMILES: c1ccc2cc(-c3ccc4ccc5c(-c6ccc7ccccc7c6)ccc6ccc3c4c65)ccc2c1]
H5
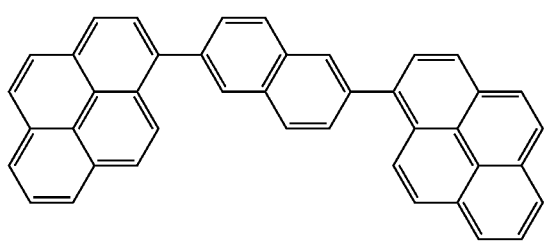 [SMILES: c1cc2ccc3ccc(-c4ccc5cc(-c6ccc7ccc8cccc9ccc6c7c89)ccc5c4)c4ccc(c1)c2c34]
H6
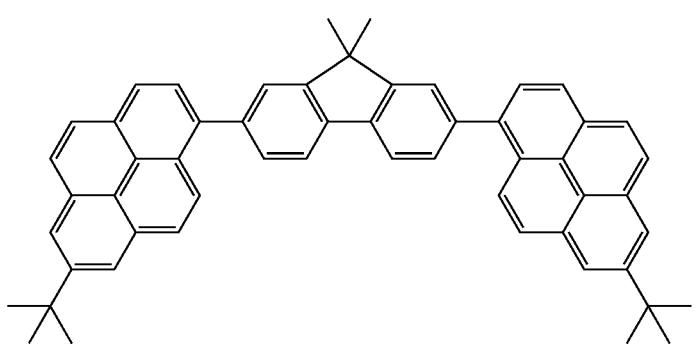 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H7

TABLE 2-continued
| | |
|---|---|
| 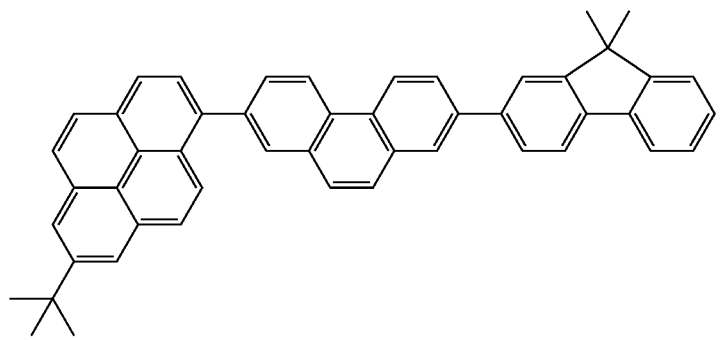 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] | H8 |
| 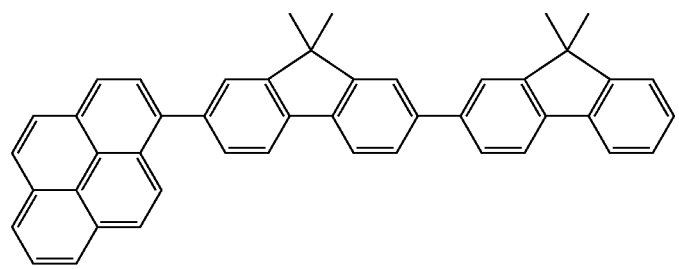 [SMILES: CC1(C)c2ccccc2-c2ccc(-c3ccc4c(c3)C(C)(C)c3cc(-c5ccc6ccc7cccc8ccc5c6c78)ccc3-4)cc21] | H9 |
| 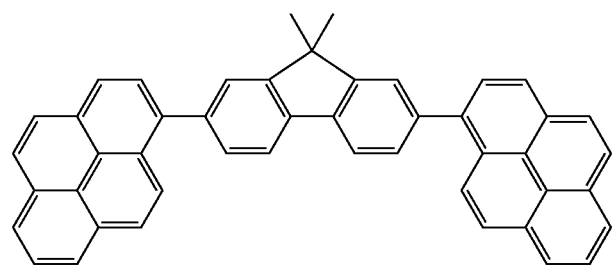 [SMILES: CC1(C)c2cc(-c3ccc4ccc5cccc6ccc3c4c56)ccc2-c2ccc(-c3ccc4ccc5cccc6ccc3c4c56)cc21] | H10 |
| 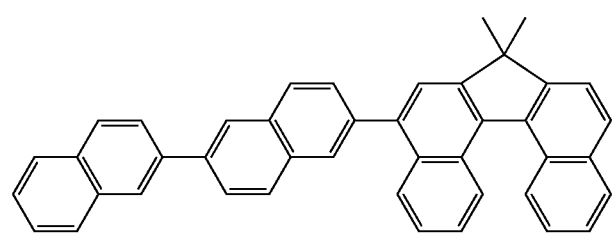 [SMILES: CC1(C)c2ccc3ccccc3c2-c2c1cc(-c1ccc3cc(-c4ccc5ccccc5c4)ccc3c1)c1ccccc21] | H11 |
| 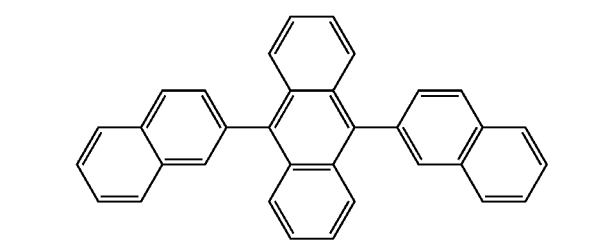 [SMILES: c1ccc2cc(-c3c4ccccc4c(-c4ccc5ccccc5c4)c4ccccc34)ccc2c1] | H12 |
| 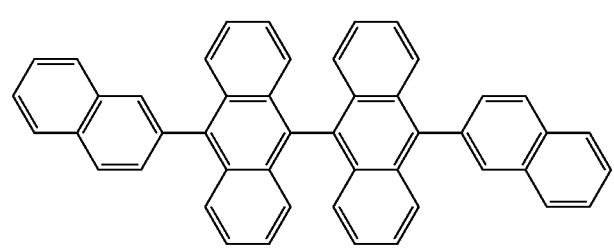 [SMILES: c1ccc2cc(-c3c4ccccc4c(-c4c5ccccc5c(-c5ccc6ccccc6c5)c5ccccc45)c4ccccc34)ccc2c1] | H13 |

TABLE 2-continued
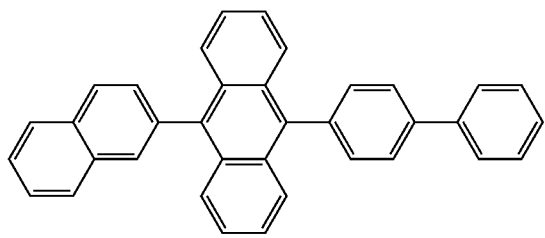 [SMILES: c1ccc(-c2ccc(-c3c4ccccc4c(-c4ccc5ccccc5c4)c4ccccc34)cc2)cc1] H14
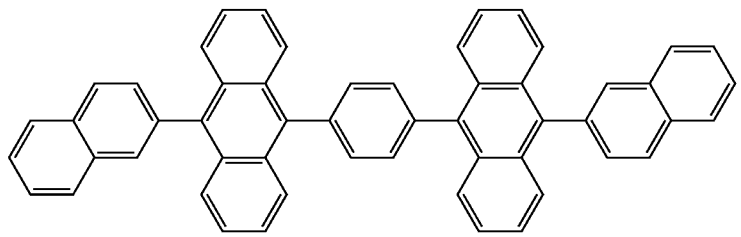 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H15
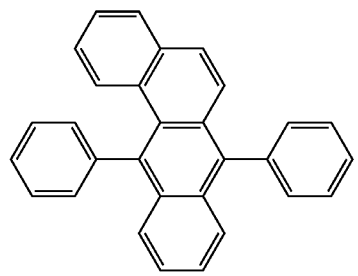 [SMILES: c1ccc(-c2c3ccccc3c(-c3ccccc3)c3c2ccc2ccccc23)cc1] H16
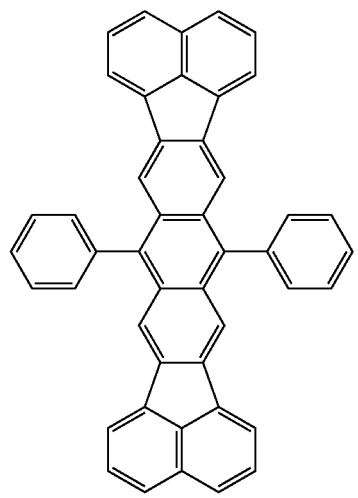 [SMILES: c1ccc(-c2c3cc4c(cc3c(-c3ccccc3)c3cc5c(cc23)-c2cccc3cccc-5c23)-c2cccc3cccc-4c23)cc1] H17
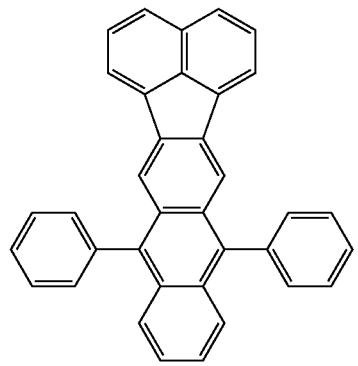 [SMILES: c1ccc(-c2c3ccccc3c(-c3ccccc3)c3cc4c(cc23)-c2cccc3cccc-4c23)cc1] H18

TABLE 2-continued
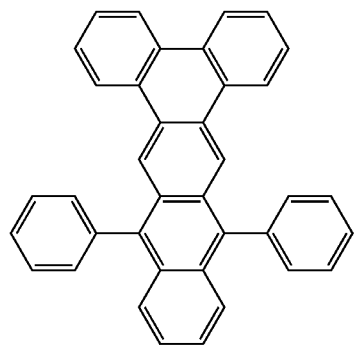 [SMILES: c1ccc(-c2c3ccccc3c(-c3ccccc3)c3cc4c5ccccc5c5ccccc5c4cc23)cc1]
H19
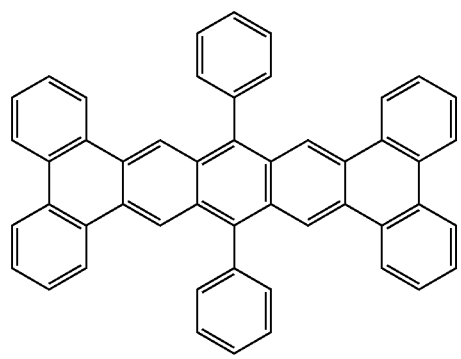 [SMILES: c1ccc(-c2c3cc4c5ccccc5c5ccccc5c4cc3c(-c3ccccc3)c3cc4c5ccccc5c5ccccc5c4cc23)cc1]
H20
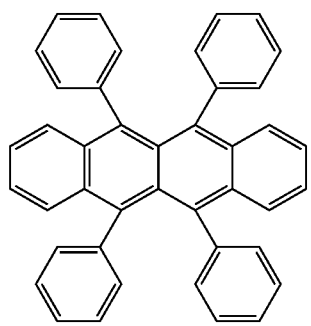 [SMILES: c1ccc(-c2c3ccccc3c(-c3ccccc3)c3c(-c4ccccc4)c4ccccc4c(-c4ccccc4)c23)cc1]
H21
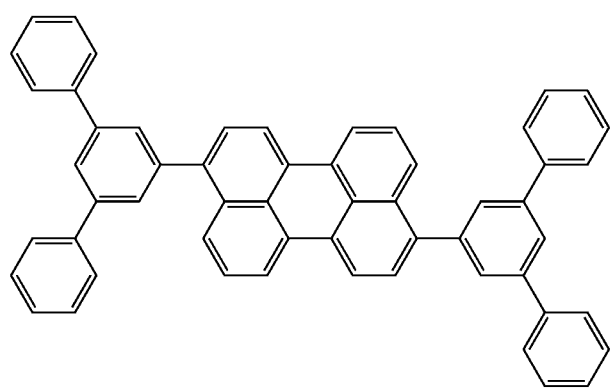 [SMILES: c1ccc(-c2cc(-c3ccccc3)cc(-c3ccc4c5cccc6c(-c7cc(-c8ccccc8)cc(-c8ccccc8)c7)ccc(c7cccc3c74)c65)c2)cc1]
H22

TABLE 2-continued

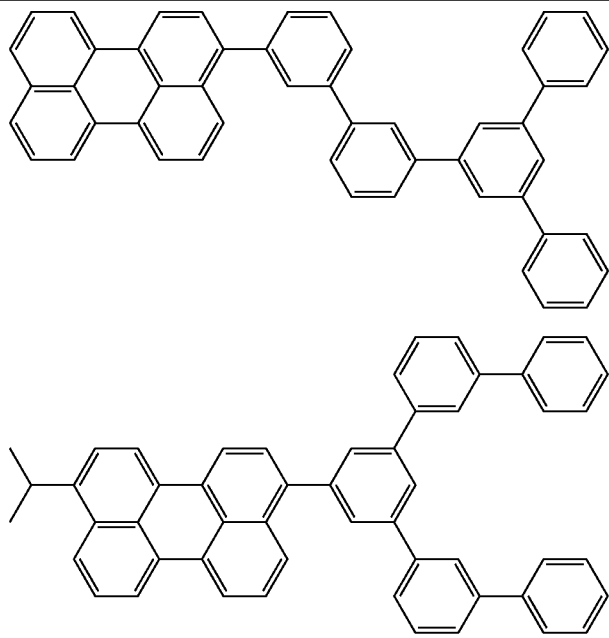

However, aspects of the present invention are not limited thereto. Derivatives of the compounds shown in Table 2 may also be used as the host material.

Besides the compounds mentioned above, for example, there may also be mentioned a condensed polycyclic compound (such as a fluorene derivative, a naphthalene derivative, an anthracene derivative, a pyrene derivative, a carbazole derivative, a quinoxaline derivative, or a quinoline derivative), an organic aluminum complex such as tris(8-quinolate) aluminum, an organic zinc complex, a triphenylamine derivative, and a polymer derivative, such as a polyfluorene derivative, or a polyphenylene derivative. Of course, the host material is not limited to those mentioned above.

As the light emitting material which can be used besides the condensed polycyclic compound according to aspects of the present invention, for example, there may be mentioned a condensed polycyclic compound (such as a fluorene derivative, a naphthalene derivative, a pyrene derivative, a perylene derivative, a tetracene derivative, an anthracene derivative, or rubrene), a quinacridone derivative, a coumarin derivative, a stilbene derivative, and an organic aluminum complex such as tris(8-quinolate)aluminum, and in addition, a phosphorescence light emitting metal complex, such as an iridium complex, a platinum complex, a terbium complex, or a europium complex, may also be mentioned. However, of course, the light emitting material is not limited to those mentioned above.

As the electron injection/transport material, a material may be arbitrarily selected from materials in which electrons from the cathode can be easily injected and which can transport injected electrons to the light emitting layer and may also be selected in consideration, for example, of the balance with the hole mobility of the hole injection/transport material.

As a material having an electron injection/transport ability, for example, there may be mentioned an oxadiazole derivative, an oxazole derivative, a pyrazine derivative, a triazole derivative, a triazine derivative, a quinoline derivative, a quinoxaline derivative, a phenanthroline derivative, and an organic aluminum complex.

A material having a higher work function may be used as an anode material.

For example, a metal itself, such as gold, platinum, silver, copper, nickel, palladium, cobalt, selenium, vanadium, or tungsten, an alloy thereof, and a metal oxide, such as tin oxide, zinc oxide, indium oxide, indium tin oxide (ITO), or indium zinc oxide, may be used.

In addition, conductive polymers, such as a polyaniline, a polypyrrole, and a polythiophene, may also be used.

These electrode materials may be used alone, or at least two types thereof may also be used in combination. In addition, the anode may be formed from one layer or a plurality of layers.

On the other hand, a material having a low work function may be used as a cathode material. For example, an alkali metal such as lithium, an alkaline earth metal, such as calcium, and a metal itself, such as aluminum, titanium, manganese, silver, lead, or chromium, may be mentioned. Alternatively, an alloy formed in combination of the above metals may also be used.

For example, magnesium-silver, aluminum-lithium, and aluminum-magnesium may be used. A metal oxide, such as indium tin oxide (ITO), may also be used. These electrode materials may be used alone, or at least two types thereof may also be used in combination. In addition, the cathode may be formed from one layer or a plurality of layers.

In the organic light emitting element according to this embodiment, a layer containing the organic compound according to aspects of the present invention and a layer containing the other organic compound are each formed by the following method.

As a method for forming the organic compound layer, for example, there may be mentioned a vacuum deposition method, an ionized deposition method, a sputtering method, a plasma method, or a known coating method (such as a spin coating method, a dipping method, a casting method, an LB method, or an ink jet method) in which the organic compound is dissolved in an appropriate solvent.

When the layer is formed by a vacuum deposition method, a solution coating method, or the like, for example, crystallization is not likely to occur, and an excellent aging stability can be obtained. In addition, when film formation is performed by a coating method, a film may also be formed in combination with an appropriate binder resin.

As the above binder resin, although a poly(vinyl carbazole) resin, a polycarbonate resin, a polyester resin, an ABS resin, an acrylic resin, a polyimide resin, a phenol resin, an epoxy resin, a silicone resin, and an urea resin may be mentioned by way of example, the binder resin is not limited thereto.

In addition, these binder resins may be used alone as a homopolymer or a copolymer, or at least two types thereof may be used in combination. Furthermore, optionally, additives, such as a known plasticizer, antioxidant, and ultraviolet absorber, may also be used together.

(Application of Organic Light Emitting Element According to this Embodiment)

The organic light emitting element according to this embodiment may be used for a display device and a lighting device. In addition, the organic light emitting element according to this embodiment may also be used, for example, for an exposure light source of an image forming device of an electrophotographic system and a backlight of a liquid crystal display device.

The display device has the organic light emitting element according to this embodiment in a display portion. This display portion has a plurality of pixels. This pixel has the organic light emitting element according to this embodiment and an active element. As the active element, for example, a switching element or an amplifying element may be mentioned, and in particular, a transistor or an MIM element may be mentioned.

A drain electrode or a source electrode of the transistor is connected to the anode or the cathode of this organic light emitting element.

The display device may be used as an image display device of a personal computer (PC), a head mount display, a mobile phone, or the like. As an image to be displayed, any image, such as a two-dimensional image or a three-dimensional image, may be displayed.

The display device may be an image information processing device which has an image input portion to input image information from an area CCD, a linear CCD, a memory card, or the like, and which outputs an input image on the display portion.

The image information processing device may be a digital camera having an imaging optical system in which the image input portion is formed of an imaging element, such as a CCD sensor.

The display device may have an input function which can perform an input by touching an output image. For example, a touch-panel function may be mentioned.

In addition, the display device may also be used for a display portion of a multifunctional printer.

The organic light emitting element according to this embodiment may also be used for a lighting device. This lighting device has the organic light emitting element according to this embodiment and an AC/DC converter to supply a drive voltage thereto.

The color of light emitted from the lighting device according to this embodiment may be white, natural white, and any other colors.

In order to emit white light, the structure is formed in such a way that the light emitting portion of the organic light emitting element has a plurality of light emitting layers, the condensed polycyclic compound according to aspects of the present invention emits green light, and the other layers emit light other than the green light, so that the element emits white light.

The organic light emitting element according to this embodiment may be used for an exposure light source of an image forming device. The image forming device has a photo conductor, a charging portion to charge the photo conductor, an exposure portion to expose the photo conductor, and a developing unit to develop an electrostatic latent image. The organic light emitting element is used for the exposure portion.

The exposure light source has a plurality of light emitting points which are arranged to form at least one line. In addition, the light quantity of each of the light emitting points is independently controlled. These light emitting points are each formed of the organic light emitting element according to aspects of the present invention.

Figure 2:
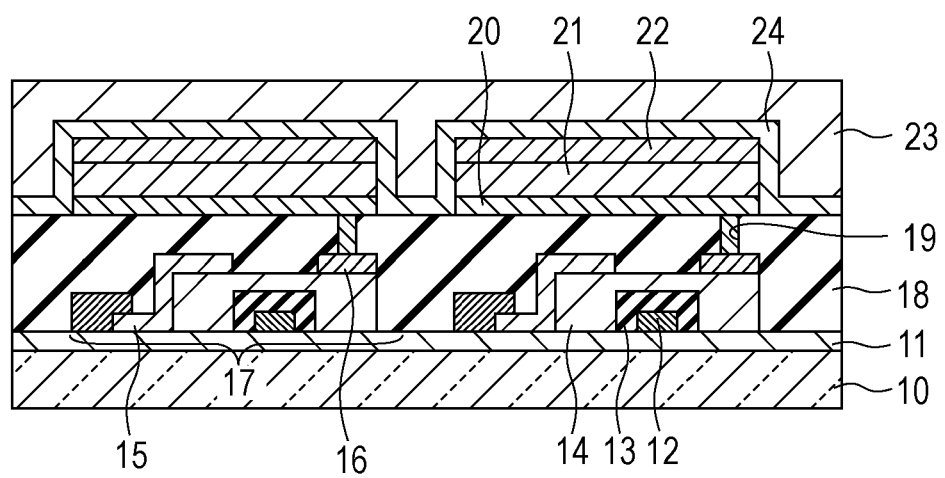
FIG. 2 is a schematic cross-sectional view showing the organic light emitting element according to the embodiment and a switching element connected thereto.

FIG. 2 is a schematic cross-sectional view of a display device having the organic light emitting element according to this embodiment and a TFT element, which is one example of the transistor, connected thereto.

This display device includes a substrate 10 formed of a glass or the like and a dampproof film 11 provided thereon to protect the TFT element or the organic compound layer. In addition, reference numeral 12 indicates a metal gate electrode. Reference numeral 13 indicates a gate insulating film, and reference numeral 14 indicates a semiconductor layer.

A TFT element 17 includes the semiconductor layer 14, a drain electrode 15, and a source electrode 16. An insulating film 18 is provided on an upper portion of the TFT 17. An anode 20 of the organic light emitting element and the source electrode 16 are connected to each other through a contact hole 19.

The structure of the display device according to this embodiment is not limited to that described above and may have any structure as long as the anode or the cathode is connected to one of the source electrode and the drain electrode of the TFT element.

In this figure, although it is shown as if an organic compound layer 21 is a single organic compound layer, a plurality of layers may form the organic compound layer 21. On a cathode 22, a first protective layer 23 and a second protective layer 24 are provided to suppress degradation of the organic light emitting element.

The emission luminance of the organic light emitting element according to this embodiment is controlled by a TFT element which is one example of the switching element. When a plurality of organic light emitting elements is provided in the plane, an image can be displayed by the emission luminance of each organic light emitting element.

The switching element of the organic light emitting element according to this embodiment is not limited to a TFT element, and a common transistor or an MIM element may also be used. In addition, the control may also be performed in such a way that active matrix drivers are formed on a Si substrate or the like, and the organic light emitting elements are provided thereon.

The structure may be selected depending on the degree of fineness, and for example, when the fineness is approximately QVGA, the structure in which the organic light emitting elements are provided on a Si substrate may be provided.

When a display device using the organic light emitting element according to this embodiment is driven, stable display with excellent image quality can be performed for a long time.

EXAMPLES

Hereinafter, examples will be described. However, the present invention is not limited thereto.

Example 1

Synthesis of Intermediates 1 to 3

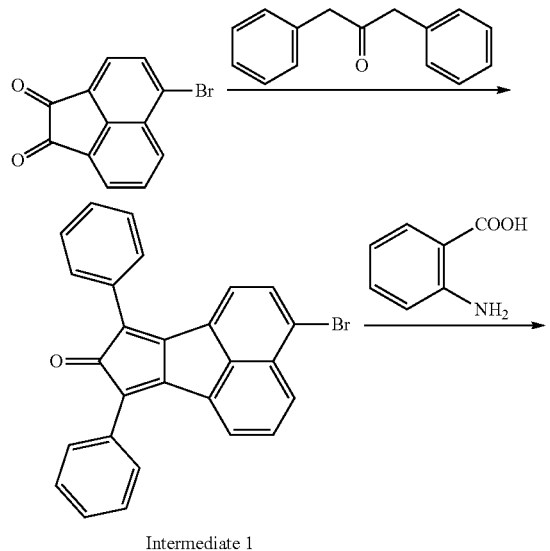

Intermediate 1

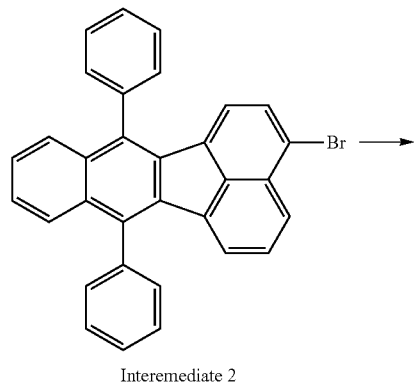

Interemediate 2

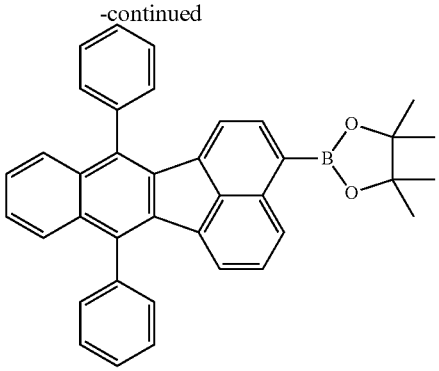

Interemediate 3

The following reagents and solvent were charged in a 200-ml recovery flask.
5-bromo-acenaphthene quinone: 2.6 g (10 mmol)
1,3-diphenyl-2-propanone: 2.1 g (10 mmol)
Ethanol: 50 ml To this reaction solution, a solution prepared by dissolving 0.31 g of potassium hydroxide in 30 ml of ethanol was dripped at 60° C. while stirring was performed. After the dripping was completed, heating was further performed for 1 hour while the reaction solution was refluxed.

After the reaction was completed, the reaction solution was cooled to room temperature and was then filtered. An obtained solid was washed with ethanol, so that 4.1 g of the intermediate 1 was obtained (yield: 95%).

Subsequently, the following reagents and solvent were charged in a 200-ml recovery flask.
Intermediate 1: 4.1 g (9.5 mmol)
Anthranilic acid: 1.6 g (11 mmol)
Isoamyl nitrite: 1.3 g (11 mmol)
Toluene: 100 ml This reaction solution was heated at 95° C. for 3 hours in a nitrogen atmosphere while stirring was performed. After the reaction was completed, the solvent was removed by reduced-pressure distillation, and a solid thus obtained was refined by a silica gel column (chloroform:heptane=1:3), so that 3.9 g of the intermediate 2 was obtained (yield: 84%).

Next, the following reagents and solvent were charged in a 100-ml recovery flask.
Intermediate 2: 2.0 g (4.1 mmol)
Bis(pinacolato)diboron: 1.3 g (5.0 mmol)
[1,1'-bis(diphenylphosphino)ferrocene]palladium(II) dichloride dichloromethane adduct: 0.33 g (0.41 mmol)
Potassium acetate: 1.3 g (13 mmol)
1,4-dioxane (dehydrated): 20 ml This reaction solution was heated and refluxed in a nitrogen atmosphere for 5 hours while stirring was performed. After the reaction was completed, a precipitated salt was removed by filtration.

The solvent of an obtained filtrate was removed by reduced-pressure distillation, and a precipitated solid was then refined by a silica gel column (chloroform:heptane=2:1), so that 1.6 g of the intermediate 3 was obtained (yield: 72%).

Synthesis of Intermediates 4 to 7

In accordance with a synthetic method disclosed in Japanese Patent Laid-Open No. 2011-11994, the intermediates 4 to 7 were synthesized. In particular, the synthesis was performed in accordance with the following scheme.

Synthesis of Intermediate 8

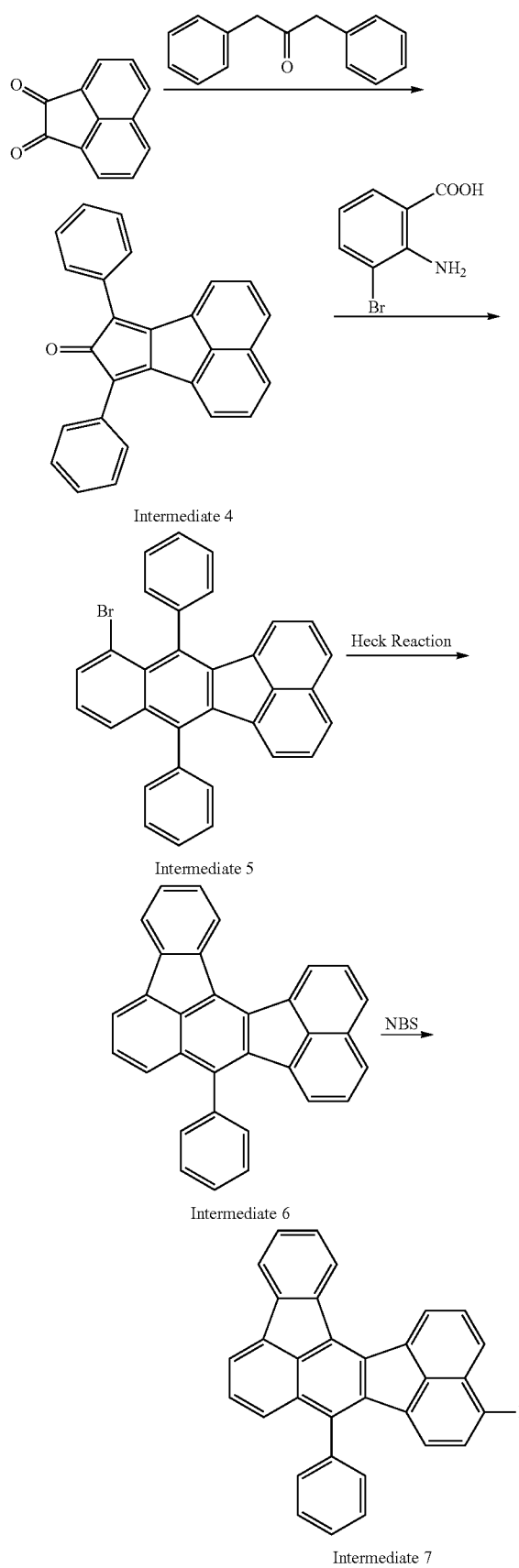

Intermediate 4

Intermediate 5

Intermediate 6

Intermediate 7

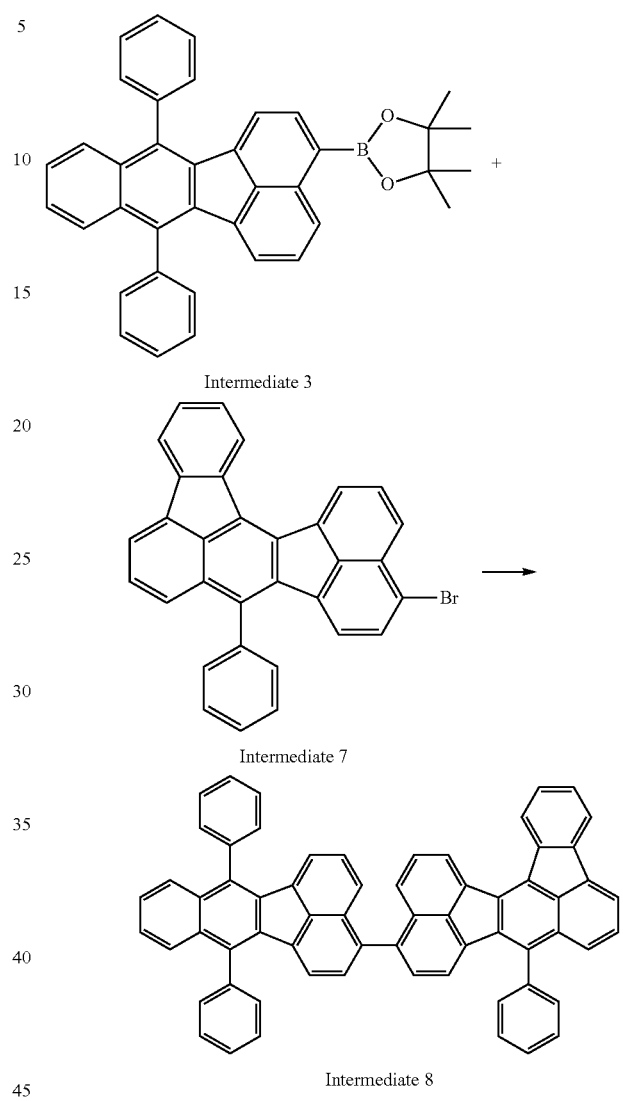

Intermediate 3

Intermediate 7

Intermediate 8

The following reagents and solvents were charged in a 50-ml recovery flask.

Intermediate 3: 1.2 g (2.3 mmol)
Intermediate 7: 1.0 g (2.1 mmol)
Tetrakis(triphenylphosphine)palladium(0): 0.24 g (0.21 mmol)
Toluene: 10 ml
Ethanol: 2 ml
2M sodium carbonate aqueous solution: 3 ml This reaction solution was heated and refluxed in a nitrogen atmosphere for 5 hours while stirring was performed. After the reaction was completed, an organic layer was separated and was dried with magnesium sulfate followed by filtration. The solvent of an obtained filtrate was removed by reduced-pressure distillation, and a solid thus obtained was then refined by a silica gel column (chloroform:heptane=1:3), so that 1.5 g of the intermediates 8 was obtained (yield: 88%).

Synthesis of Example Compound B-1

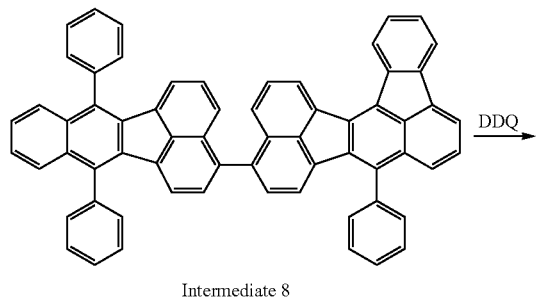

Intermediate 8

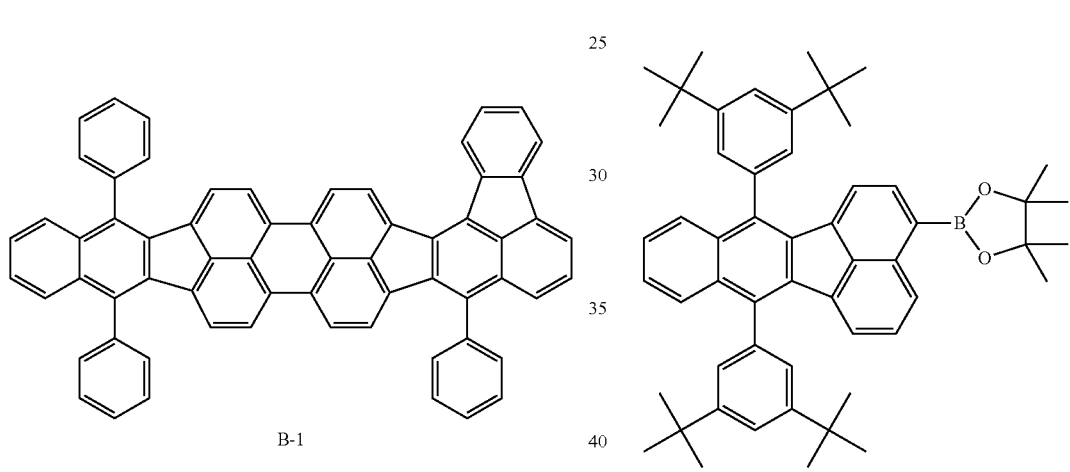

B-1

The following reagents and solvent were charged in a 200-ml recovery flask.
Intermediate 8: 0.50 g (0.62 mmol)
Boron trifluoride-diethylether complex: 0.44 g (3.1 mmol)
dichloromethane (dehydrated): 50 ml
Trifluoroacetic acid: 10 ml To this reaction solution, 0.28 g of 2,3-dichloro-5,6-dicyano-1,4-benzoquinone (DDQ) was slowly added at room temperature. After the addition was completed, stirring was performed at room temperature for 1 hour in a nitrogen atmosphere, and the dissipation of the intermediate 8 was then confirmed by a thin layer chromatography (TLC).

Subsequently, after 0.23 g of ferrocene was added to the reaction solution and was then stirred for 30 minutes, the reaction was stopped. Furthermore, after 50 ml of methanol was added to precipitate a solid, filtration was performed. After the solid thus obtained was washed with methanol, recrystallization was performed using toluene/heptane, so that 0.40 g of the example compound B-1 was obtained (yield: 80%). By MALDI-TOF MS (Matrix-Assisted Laser Desorption-Ionization Time-of-Flight Mass Spectrometry), M+ of this compound was confirmed to be 802.3.

Furthermore, the structure of this compound was confirmed by $^1$H-NMR measurement.

$^1$H-NMR (CDCl$_3$, 500 MHz) δ(ppm): 8.60 (1H, d), 8.52 (1H, d), 8.27 (1H, d), 8.03 (1H, d), 7.99 (1H, d), 7.91 (1H, d), 7.88-7.82 (2H, m), 7.75-7.49 (19H, m), 7.48-7.42 (2H, m), 7.42-7.37 (2H, m), 6.69 (1H, d), 6.64 (1H, d), 6.57 (1H, d)

In addition, the emission spectrum of a toluene diluted solution (1×10$^{-6}$ M) of the example compound B-1 was measured at an excitation wavelength of 500 nm using F-4500 manufactured by Hitachi Ltd. The maximum peak wavelength of the obtained emission spectrum was 605 nm.

Example 2

Synthesis of Intermediate 9

Intermeidate 9

Except that 1,3-diphenyl-2-propanone used for the synthesis of the intermediates 1 to 3 was changed to 1,3-bis(3,5-di-tert-butylphenyl)-2-propanone, the intermediate 9 was obtained by a method similar to that of the synthesis of the intermediate 3 of Example 1.

Synthesis of Example Compound B-4

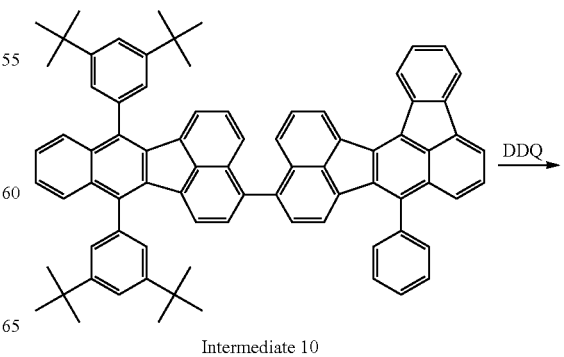

Intermediate 10

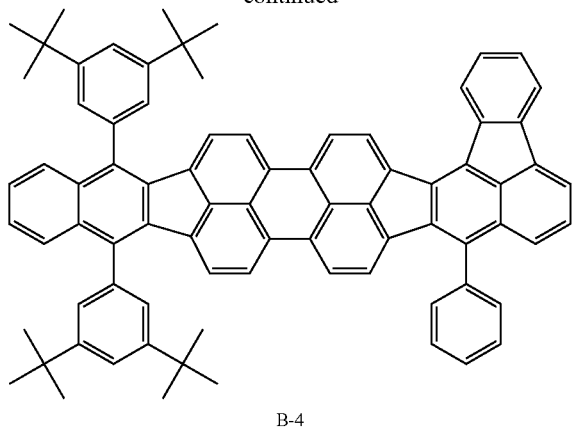

B-4

Except that the intermediate 3 used for the synthesis of the intermediate 8 was changed to the intermediate 9, the intermediate 10 was obtained by a method similar to that of the synthesis of the intermediate 8 of Example 1.

Furthermore, except that the intermediate 8 used for the synthesis of the example compound B-1 was changed to the intermediate 10, the example compound B-4 was obtained by a method similar to that of the synthesis of the example compound B-1 of Example 1.

M+ of this compound was confirmed by MALDI-TOF MS to be 1,026.5.

Furthermore, the structure of this compound was confirmed by $^1$H-NMR measurement.

$^1$H-NMR (CDCl$_3$, 500 MHz) δ(ppm): 8.66 (1H, d), 8.58 (1H, d), 8.36 (1H, d), 8.05 (1H, d), 8.01 (1H, d), 7.93 (2H, t), 7.88 (1H, d), 7.79-7.73 (2H, m), 7.71-7.61 (5H, m), 7.61-7.39 (12H, m), 6.68 (1H, d), 6.64 (1H, d), 6.56 (1H, d), 1.46 (18H, s), 1.43 (18H, s)

When the emission spectrum was measured by a method similar to that for the example compound B-1, the maximum peak wavelength was 607 nm.

Example 3

Synthesis of Intermediate 11

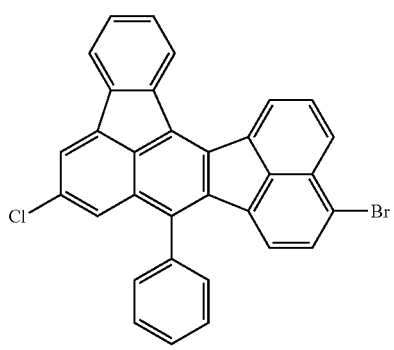

Intermediate 11

Except that 3-bromoanthranilic acid used for the synthesis of the intermediates 4 to 7 was changed to 3-bromo-5-chloroanthranilic acid, the intermediate 11 was obtained by a method similar to that of the synthesis of the intermediate 7 of Example 1.

Synthesis of Intermediate 13

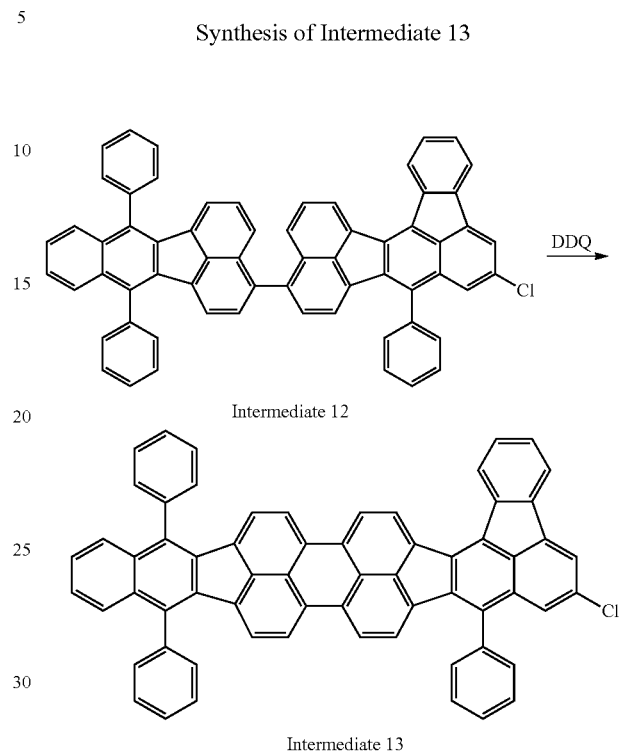

Intermediate 12

Intermediate 13

Except that the intermediate 7 used for the synthesis of the intermediate 8 was changed to the intermediate 11, the intermediate 12 was obtained by a method similar to that of the synthesis of the intermediate 8 of Example 1.

Furthermore, except that the intermediate 8 used for the synthesis of the example compound B-1 was changed to the intermediate 12, the intermediate 13 was obtained by a method similar to that of the synthesis of the example compound B-1 of Example 1.

Synthesis of Example Compound A-5

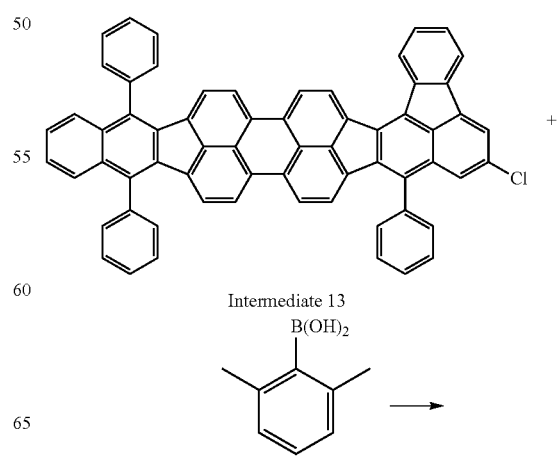

Intermediate 13

-continued

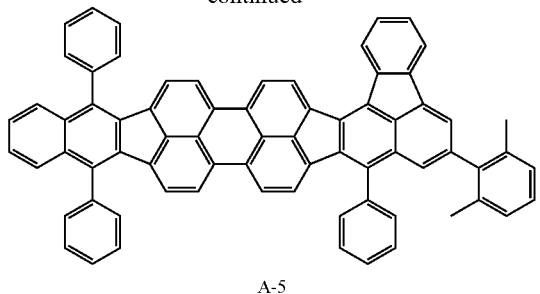

A-5

The following reagents and solvents were charged in a 50-ml recovery flask.
Intermediate 13: 0.30 g (0.36 mmol)
2,6-dimethyl phenylboronic acid (manufactured by Tokyo Chemical Industry Co., Ltd.): 0.11 g (0.72 mmol)
2-dicyclohexyl-phosphino-2',6'-dimethoxybiphenyl: 0.030 g (0.072 mmol)
Palladium acetate(II): 0.0081 g (0.036 mmol)
Toluene: 10 ml
Ethanol: 1 ml
2M tripotassium phosphate aqueous solution: 1 ml This reaction solution was heated and refluxed for 8 hours in a nitrogen atmosphere while stirring was performed. After the reaction was completed, 5 ml of methanol and 5 ml of water were added, a precipitated solid was filtrated.

After the solid thus obtained was washed with ethanol, recrystallization was performed using toluene/heptane, so that 0.22 g of the example compound A-5 was obtained (yield: 67%).

M+ of this compound was confirmed by MALDI-TOF MS to be 906.3.

When the emission spectrum was measured by a method similar to that of the example compound B-1, the maximum peak wavelength was 611 nm.

Example 4

Formation of Organic Light Emitting Element

In this example, an organic light emitting element having the structure in which an anode/hole transport layer/electron block layer/light emitting layer/hole block layer/electron transport layer/cathode were sequentially provided on a substrate in this order was formed by the following method.

An ITO film having a thickness of 100 nm formed as an anode on a glass substrate by a sputtering method was used as a transparent conductive support substrate (ITO substrate).

The following organic compound layers and electrode layers were successively formed on this ITO substrate using vacuum deposition performed by resistance heating in a vacuum chamber at a pressure of $10^{-5}$ Pa.

In this case, the electrode surfaces facing each other were each formed to have an area of 3 mm$^2$.
Hole transport layer (30 nm) HTL-1
Electron block layer (10 nm) EBL-1
Light emitting layer (30 nm) Host material: H6 (60 percent by weight), Assist material: H22 (39.5 percent by weight), Guest material: B-1 (0.5 percent by weight)
Hole block layer (10 nm) HBL-1
Electron transport layer (30 nm) ETL-1
Metal electrode layer 1 (1 nm) LiF
Metal electrode layer 2 (100 nm) Al

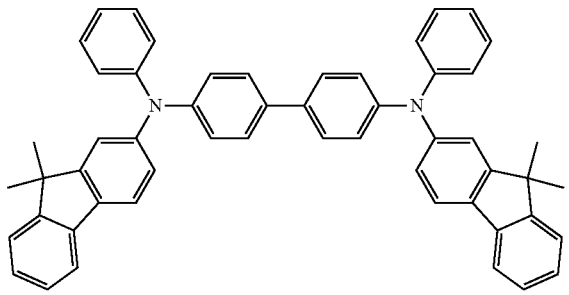

HTL-1

EBL-1

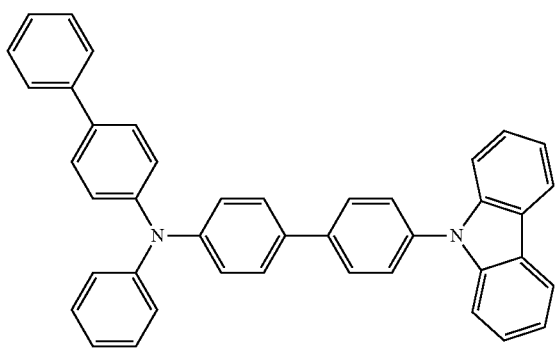

HBL-1

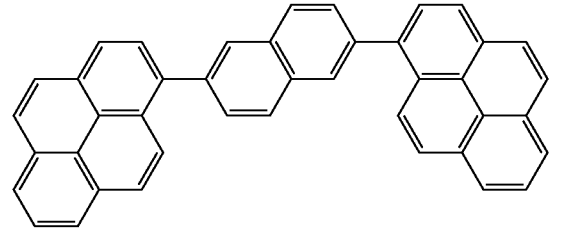

ETL-1

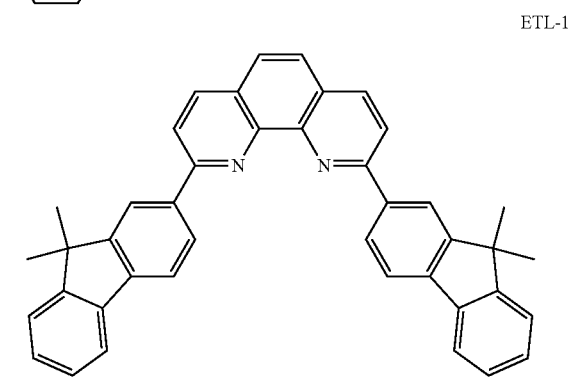

Next, in order to prevent element degradation of the organic light emitting element caused by absorption of moisture, a protective glass plate was placed in a dry air atmosphere to cover the organic light emitting element and was sealed with an acrylic resin adhesive. The organic light emitting element was obtained as described above.

The current-voltage characteristic of the obtained organic light emitting element was measured with a pA meter 4140B manufactured by Hewlett-Packard Company, and the emission luminance of the above element was measured using BM7-fast manufactured by Topcon Corporation.

When the ITO electrode was used as a positive electrode, the Al electrode was used as a negative electrode, and a voltage of 4.1 V was applied therebetween, red light emission having a light emitting efficiency of 3.2 cd/A was observed.

In addition, in this element, the CIE chromaticity coordinates (x, y) were (0.67, 0.31), and red light having a high color purity was observed.

When the luminance of the element was measured after a current of 40 mA/cm$^2$ was further passed for 100 hours, the reduction rate from the initial luminance was 5% or less.

Examples 5 and 6

Except that the host material, the assistant material, and the guest material were changed, elements were formed by a method similar to that of Example 4.

In addition, when the elements thus obtained were evaluated in a manner similar to that of Example 4, red light emission was observed from each element. The light emitting efficiency and the applied voltage are shown in Table 3.

Furthermore, when the luminance of each element was measured after a current of 40 mA/cm$^2$ was further passed for 100 hours, the reduction rate of each element from the initial luminance was 5% or less.

TABLE 3

| | HOST MATERIAL | ASSIST MATERIAL | GUEST MATERIAL | LIGHT EMITTING EFFICIENCY (cd/A) | VOLTAGE (V) |
|---|---|---|---|---|---|
| EXAMPLE 5 | H12 | H21 | B-4 | 3.5 | 4.1 |
| EXAMPLE 6 | H7 | H23 | A-5 | 3.0 | 4.4 |

Example 7

In this example, an organic light emitting element having the structure in which an anode/hole transport layer/electron block layer/first light emitting layer (red)/second light emitting layer (green)/third light emitting layer (blue)/hole block layer/electron transport layer/cathode were sequentially provided on a substrate was formed by the following method.

An ITO film having a thickness of 100 nm formed as an anode on a glass substrate by a sputtering method was used as a transparent conductive support substrate (ITO substrate).

The following organic compound layers and electrode layers were successively formed on this ITO substrate using vacuum deposition performed by resistance heating in a vacuum chamber at a pressure of 10$^{-5}$ Pa.

In this case, the electrode surfaces facing each other were each formed to have an area of 3 mm$^2$.

Hole transport layer (30 nm) HTL-1
Electron block layer (10 nm) EBL-1
First light emitting layer (5 nm) Host material: H6 (80 percent by weight), Assist material: H22 (19.5 percent by weight), Guest material: B-1 (0.5 percent by weight)
Second light emitting layer (7 nm) Host material: H12 (98 percent by weight), Guest material: GML-1 (2 percent by weight)
Third light emitting layer (10 nm) Host material: H12 (97 percent by weight), Guest material: BML-1 (3 percent by weight)
Hole block layer (10 nm) HBL-2
Electron transport layer (30 nm) ETL-1
Metal electrode layer 1 (1 nm) LiF
Metal electrode layer 2 (100 nm) Al

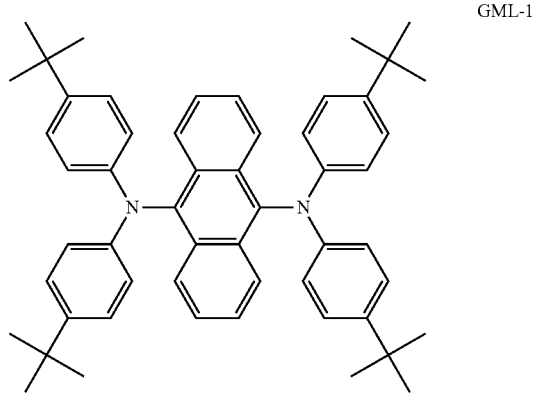

GML-1

-continued

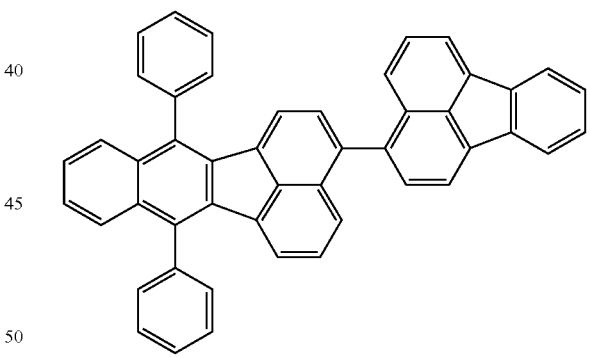

BML-1

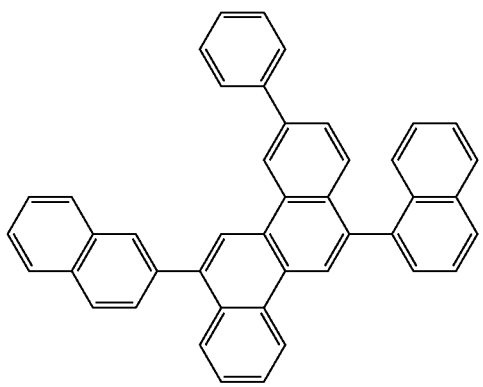

HBL-2

Next, in order to prevent element degradation of the organic light emitting element caused by absorption of moisture, a protective glass plate was placed in a dry air atmosphere to cover the organic light emitting element and was sealed with an acrylic resin adhesive. The organic light emitting element was obtained as described above.

The current-voltage characteristic of the obtained organic light emitting element was measured with a pA meter 4140B manufactured by Hewlett-Packard Company, and the emission luminance of the above element was measured using BM7-fast manufactured by Topcon Corporation.

When the ITO electrode was used as a positive electrode, the Al electrode was used as a negative electrode, and a voltage of 4.6 V was applied, white light emission having a light emitting efficiency of 9.6 cd/A was observed.

As has thus been described, it was found that when the condensed polycyclic compound according to aspects of the present invention is used as a light emitting material of an organic light emitting element, excellent light emitting efficiency and element life can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-181581 filed Aug. 23, 2011, which is hereby incorporated by reference herein in its entirety.

What is claimed is:

1. A condensed polycyclic compound represented by the following general formula [1]

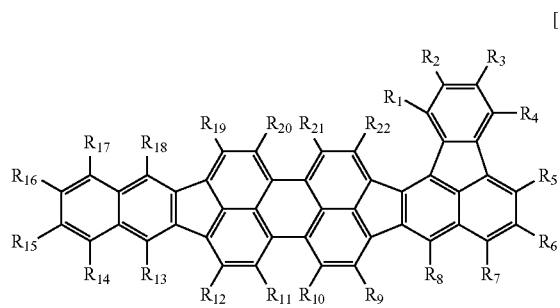

[1]

where in the formula [1], $R_1$ to $R_{22}$ are each independently selected from the group consisting of a hydrogen atom, a substituted or unsubstituted alkyl group, a substituted or unsubstituted aryl group, and a substituted or unsubstituted heterocyclic group.

2. The condensed polycyclic compound according to claim 1, wherein in the general formula [1], $R_7$, $R_9$ to $R_{12}$, $R_{14}$, $R_{17}$, and $R_{19}$ to $R_{22}$ each indicate a hydrogen atom.

3. The condensed polycyclic compound according to claim 1, wherein in the general formula [1], $R_5$ to $R_2$, $R_9$ to $R_{12}$, $R_{14}$ to $R_{17}$, and $R_{19}$ to $R_{22}$ each indicate a hydrogen atom.

4. The condensed polycyclic compound according to claim 1, wherein in the general formula [1], $R_6$, $R_8$, $R_{13}$, and $R_{18}$ each indicate the aryl group.

5. The condensed polycyclic compound according to claim 1, wherein in the general formula [1], $R_6$, $R_8$, $R_{13}$, and $R_{18}$ each indicate a substituted or unsubstituted phenyl group.

6. An organic light emitting element comprising:
an anode;
a cathode; and
an organic compound layer arranged therebetween,
wherein the organic compound layer contains the condensed polycyclic compound according to claim 1.

7. The organic light emitting element according to claim 6, wherein the organic compound layer includes a light emitting layer, and
the light emitting layer contains the condensed polycyclic compound.

8. The organic light emitting element according to claim 6, wherein the organic compound layer is a light emitting layer containing a host material and a guest material, and
the guest material includes the condensed polycyclic compound.

9. The organic light emitting element according to claim 6, wherein the organic compound layer includes a plurality of light emitting layers,
at least one of the light emitting layers contains the condensed polycyclic compound, and
the light emitting layers emit different types of color light from each other so as to emit white light.

10. A display device comprising:
a plurality of pixels,
wherein at least one of the pixels includes the organic light emitting element according to claim 6 and an active element connected thereto.

11. An image information processing device comprising:
a display portion to display an image; and
an input portion to input image information,
wherein the display portion includes the display device according to claim 10.

12. A lighting device comprising:
the organic light emitting element according to claim 6; and
an AC/DC converter to supply a drive voltage thereto.

13. An image forming device comprising:
a photo conductor;
a charging portion to charge a surface of the photo conductor;
an exposure portion to expose the photo conductor; and
a developing unit to develop an electrostatic latent image formed on the photo conductor,
wherein the exposure portion includes the organic light emitting element according to claim 6.

14. An exposure light source to expose a photo conductor comprising:
a plurality of light emitting points,
wherein the light emitting points are arranged to form at least one line,
the light quantity of each of the light emitting points is independently controlled, and
the light emitting points each include the organic light emitting element according to claim 6.

* * * * *